United States Patent [19]
Bini

[11] Patent Number: 5,830,468
[45] Date of Patent: Nov. 3, 1998

[54] FIBRIN(OGEN) DEGRADATION BY FIBRINOLYTIC MATRIX METALLOPROTEINASE

[75] Inventor: Alessandra Bini, New York, N.Y.

[73] Assignee: The New York Blood Center, Inc., New York, N.Y.

[21] Appl. No.: 446,887

[22] Filed: May 17, 1995

[51] Int. Cl.$^6$ ............... A61K 38/48; C12N 9/50; B65D 51/24; A61M 5/00
[52] U.S. Cl. .................. 424/94.67; 424/94.63; 424/94.1; 435/219; 530/389.3; 206/210; 604/173
[58] Field of Search .............. 424/94.67, 94.64, 424/94.1, 93.21; 206/210; 604/173; 530/389.3; 435/219

[56] References Cited

U.S. PATENT DOCUMENTS

| | | | |
|---|---|---|---|
| 4,610,879 | 9/1986 | Markland, Jr. et al. | 424/94 |
| 4,813,538 | 3/1989 | Blackman | 206/210 |
| 5,130,143 | 7/1992 | Strickland et al. | 424/94.64 |
| 5,185,001 | 2/1993 | Galanakis | 604/5 |
| 5,202,121 | 4/1993 | Pohl et al. | 424/94.64 |
| 5,260,059 | 11/1993 | Acott et al. | 424/94.67 |
| 5,260,060 | 11/1993 | Markland, Jr. et al. | 424/94.67 |
| 5,324,634 | 6/1994 | Zucker | 435/7.23 |

OTHER PUBLICATIONS

Francis CW, and Marder VJ, "Physiologic regulation and pathologic disorders of fibrinolysis", Chapter 54 in *Hemostasis and Thrombosis: Basic Principles and Clinical Practice*, 3rd ed., Colman RW, Hirsh J, Marder VJ, and Salzman EW, eds., JB Lippincott Co, Philadelphia (1994).
Collen D, "On the regulation and control of fibrinolysis", *Thromb Haemost* 43:77–89 (1980).
Collen D, and Lijnen HR, "Basic and clinical aspects of fibrinolysis and thrombolysis", *Blood* 3114–24 (1991).
Murphy G, Atkinson S, Ward R, Gavrilovic J, and Reynolds JJ, "The role of plasminogen activators in the regulation of connective tissue metalloproteinases", *Ann NY Acad Sci*, 667:1–12 (1992).
Singer et al., "VDIPEN, A Metalloproteinase-generated Neoepitope, Is Induced and Immunolocalized in Articular Cartilage during Inflammatory Arthritis", *The Journal of Clinical Investigation, Inc.*, 95:2178–2186 (1995).
Martin GV, Kennedy JW, and Marder VJ, "Thrombolytic therapy for coronary artery disease", Chapter 73 in *Hemostasis and Thrombosis: Basic Principles and Clinical Practice*, 3rd ed., Colman RW, Hirsh J, Marder VJ, and Salzman EW, eds., JB Lippincott Co, Philadelphia (1994).
Glick, BR and Pasternak JJ, "Molecular Biotechnology:Principles and Applications of Recombinant DNA", Chapter 17, pp. 403–420 (1994).
Collen D, "Biological properties of plasminogen activators", Chapter 1 in Sobel BE, Collen D, and Grossbard EB, eds., *Tissue Plasminogen Activator in Thrombolytic therapy*, Marcel Dekker, Inc., New York (1987).

Lee SW, Kahn ML, and Dichek DA, "Control of clot lysis by gene transfer", *Trends Cardiovasc Med* 3:61–66 (1993).
Purves L, Purves M, and Brandt W, "Cleavage of fibrin–derived D–dimer into monomers by endopeptidase from puff adder venom (*Bitis arietans*) acting at cross–linked sites of the γ–chain. Sequence of carboxy–terminal cyanogen bromide γ–chain fragments", *Biochemistry* 26:4640–46 (1987).
Retzios AD, and Markland FS Jr, "Purification, characterization, and fibrinogen cleavage sites of three fibrinolytic enzymes from the venom of *Crotalus basiliscus basiliscus*", *Biochemistry* 31:4547–57 (1992).
Sanchez EF, Magalhes A, Mandelbaum FR, and Diniz CR, "Purification and characterization of the hemorrhagic factor II from the venom of the Bushmaster snake (*Lachesis muta muta*)", *Biochim Biophys Acta* 1074:347–56 (1991).
Nagase H, Barrett AJ, and Woessner JF Jr, "Nomenclature and glossary of the matrix metalloproteinases", *Matrix*, Supplement No. 1:421–24 (1992).
Zavalova LL, Kuzina EV, Levina NB, and Baskova IP, "Monomerization of fragment DD by destabilase from the medicinal leech does not alter the N–terminal sequence of the γ–chain", *Thrombosis Res* 71:241–44 (1993).
Budzynski AZ, "Interaction of hementin with fibrinogen and fibrin", *Blood Coagulation and Fibrinolysis* 2:149–52 (1991).
Loewy AG, Santer UV, Wieczorek M, Blodgett JK, Jones SW, and Cheronis JC, "Purification and characterization of a novel zinc–proteinase from cultures of *Aeromonas hydrophila*", *J Biol Chem* 268:9071–78 (1993).
Cawston T, "Metalloproteinase inhibitors—Crystal gazing for a future therapy", *Br J Rheumatol* 30:242–44 (1991).
Kleiner DE Jr, and Stetler–Stevenson WG, "Structural biochemistry and activation of matrix metalloproteinases", *Curr Opin Cell Biol* 5:891–97 (1993).
Matrisian LM, "The matrix–degrading metalloproteinases", *BioEssays* 14:455–63 (1992).
Nagase H, Enghild JJ, Suzuki K, and Salvesen G, "Stepwise activation mechanisms of the precursor of matrix metalloproteinase 3 (stromelysin) by proteases and (4–aminophenyl)mercuric acetate", *Biochemistry* 29:5783–89 (1990).

(List continued on next page.)

Primary Examiner—Stephen Walsh
Assistant Examiner—Elizabeth C. Kemmerer
Attorney, Agent, or Firm—Hoffmann & Baron, LLP

[57] ABSTRACT

The invention provides a method of causing the degradation of fibrin(ogen) (i.e., fibrin, fibrinogen, and related substances) by means of a fibrinolytic metalloproteinase, such as MMP-3. The method of the invention may be performed in vitro to provide diagnostic information characterizing fibrin(ogen) and the fibrinolytic physiology. The method may also be performed in vivo as a method of thrombolytic therapy in which a fibrinolytic metalloproteinase is administered to a subject to degrade thrombus in situ. The invention further provides compositions containing a fibrinolytic metalloproteinase for the performance of fibrinolytic or thrombolytic procedures. Also provided are kits which include a fibrinolytic metalloproteinase for performing fibrinolytic or thrombolytic procedures.

30 Claims, 10 Drawing Sheets

OTHER PUBLICATIONS

Nagase H, Ogota Y, Suzuki K, Enghild JJ, and Salvesen G, "Substrate specificities and activation mechanisms of matrix metalloproteinases", *Biochem Soc Trans* 19:715–18 (1991).

Henney AM, Wakeley PR, Davies MJ, Foster K, Hembry R, Murphy G, and Humphries S, "Localization of stromelysin gene expression in atherosclerotic plaques by in situ hybridization", *Proc Natl Acad Sci USA* 88:8154–58 (1991).

Galis ZS, Sukhova GK, Lark MW, and Libby P, "Increased expression of matrix metalloproteinases and matrix degrading activity in vulnerable regions of human atherosclerotic plaques", *J. Clin Invest* 94:2493–2503 (1994).

Doolittle RF, "Fibrinogen and fibrin", in Bloom AL, and Thomas DP, eds., *Hemostasis and Thrombosis* Churchill Livingston, Edinburgh, New York (1987).

Fu Y, and Grieninger G, "$Fib_{420}$: A normal human variant of fibrinogen with two extended $\alpha$ chains", *Proc Natl Acad Sci USA* 91:2625–28 (1994).

Gabriel DA, Muga K, and Boothroyd EM, "The effect of fibrin structure on fibrinolysis", *J Biol Chem* 267:24259–63 (1992).

Kudryk BJ, Grossman ZD, McAfee JG, and Rosebrough SF, "Monoclonal antibodies as probes for fibrin(ogen) proteolysis", Chapter 19 in *Monoclonal Antibodies in Immunoscintigraphy*, Chatal J–F, ed., CRC Press, Boca Raton (1989).

Bini A, Mesa–Tejada RM, Fenoglio J, Kudryk B, and Kaplan KL, "Immunohistochemical Characterization of Fibrin(ogen)–Related Antigens in Human Tissues Using Monoclonal Antibodies", *Laboratory Investigation*, 60:814–821 (1989).

Bini A, Callender S, Pocyk R, Blombäck B, and Kudryk BJ, "Flow and antibody binding properties of hydrated fibrins prepared from plasma, platelet rich plasma and whole blood", *Thrombosis Res* 76:145–56 (1994).

Okada Y, Nagase H, and Harris ED, Jr., "A metalloproteinases from human rheumatoid synovial fibroblasts that digests connective tissue matrix components", *J Biol Chem* 261:14245–55 (1986).

Tyagi SC, Ratajska A, and Weber LT, "Myocardial matrix metalloproteinase(s):localization and activation", *Mol Cell Biochem*, 126:49–59 (1993).

Bini A and Kudryk BJ, "Fibrin and Its Derivatives in the Normal and Diseased Vessel Wall", in *Plasminogen Activation in Fibrinolysis, in Tissue Remodeling and in Development*, *Ann NY Acad Sci*, 667:112–126 (1992).

Bini A, Fenoglio J, Sobel J, Owen J, Fejgl M, and Kaplan KL, "Immunochemical Characterization of Fibrinogen, Fibrin I, and Fibrin II in Human Thrombi and Atherosclerotic Lesions", *Blood*, 69:1038–1045 (1987).

Bini A, Fenoglio J, Mesa–Tejada RM, Kudryk B, and Kaplan KL, "Identification and Distribution of Fibrinogen, Fibrin, and Fibrin(ogen) Degradation Products in Atherosclerosis, Use of Monoclonal Antibodies", *Arteriosclerosis*, 9:109–121 (1989).

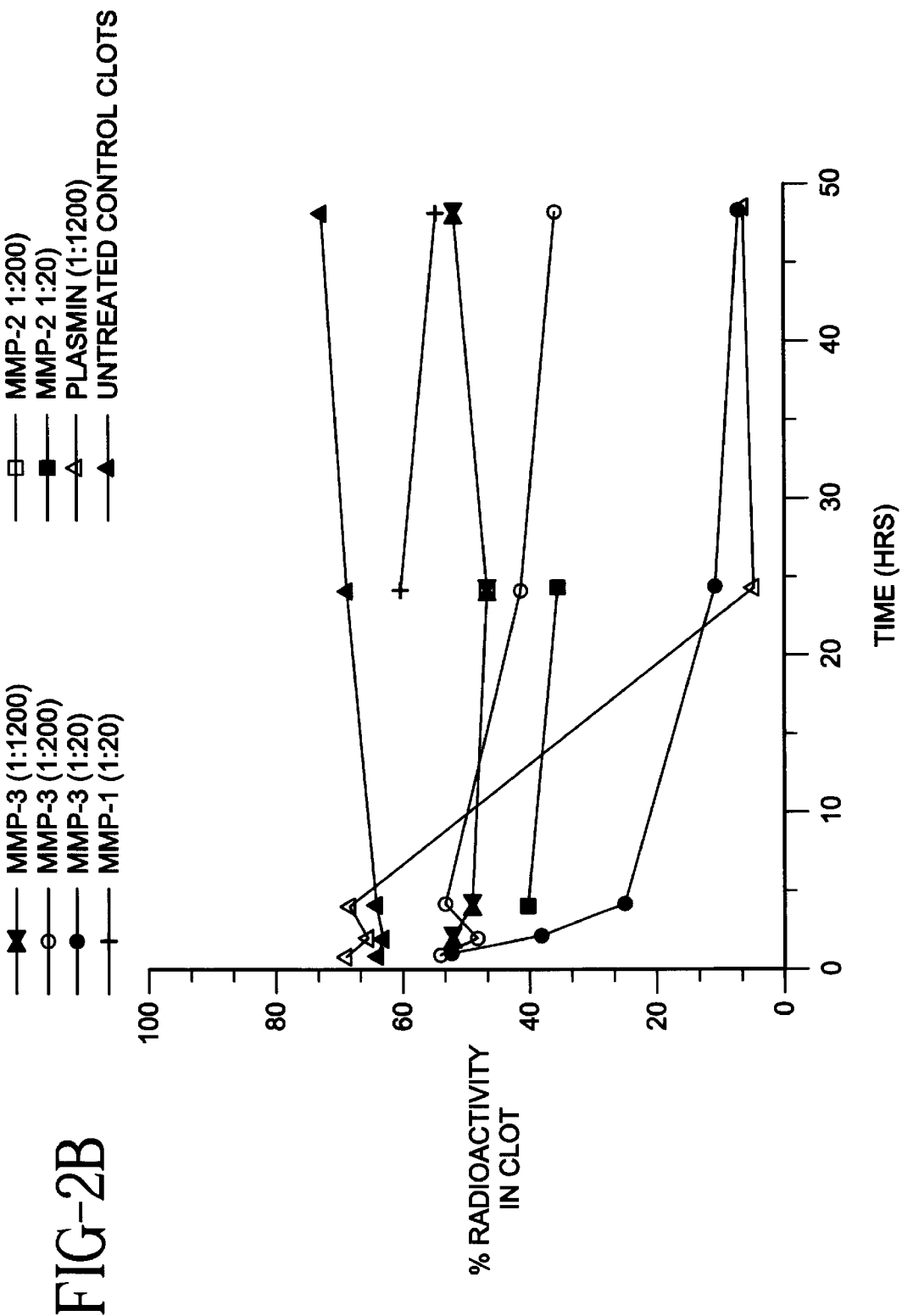

FIBRIN(OGEN) DEGRADATION BY FIBRINOLYTIC MATRIX METALLOPROTEINASE

BACKGROUND OF THE INVENTION

This invention relates to a method of enzyme-mediated breakdown of fibrinogen and fibrin. More particularly, the invention relates to a method for degrading fibrinogen and causing lysis of fibrin clots through mediation by a fibrinolytic matrix metalloproteinase. The invention further relates to the use of fibrinolytic metalloproteinase as an antithrombotic to reconstruct stenotic vessels and remove fibrin deposits.

The clotting of blood is part of the body's natural response to injury or trauma. Blood clot formation derives from a series of events called the coagulation cascade, in which the final steps involve the formation of the enzyme thrombin. Thrombin converts circulating fibrinogen into fibrin, a mesh-like structure which forms the insoluble framework of the blood clot. As a part of hemostasis, clot formation is often a life-saving process in response to trauma and serves to arrest the flow of blood from severed vasculature.

The life-saving process of clot production in response to an injury can become life-threatening when it occurs at inappropriate places in the body. For example, a clot can obstruct a blood vessel and stop the supply of blood to an organ or other body part. In addition, the deposition of fibrin contributes to partial or complete stenosis of blood vessels, resulting in chronic diminution of blood flow. Equally life-threatening are clots that become detached from their original sites and flow through the circulatory system causing blockages at remote sites. Such clots are known as embolisms. Indeed, pathologies of blood coagulation, such as heart attacks, strokes, and the like, have been estimated to account for approximately fifty percent of all hospital deaths.

The formation of fibrin during inflammation, tissue repair, or hemostasis, plays only a temporary role and must be removed when normal tissue structure and function is restored. Thus, a fibrin clot that forms quickly to stop hemorrhage in an injured blood vessel is remodeled and then removed to restore normal blood flow as healing occurs. The system responsible for fibrin breakdown and clot removal is the fibrinolytic system. Action of the fibrinolytic system is tightly coordinated through the interaction of activators, zymogens, enzymes, as well as through inhibitors of each of these components, to provide focused local activation at sites of fibrin deposition (Refs. 1–3).

The principal mediator of fibrinolysis is plasmin, a trypsin-like endopeptidase which cleaves fibrin to dissolve clots and to permit injured tissues to regenerate. Plasmin has also been demonstrated to play a role in degrading proteins involved in cell-cell and cell-matrix interactions, as well as in activating other tissue remodeling enzymes such as metalloproteinases (Ref. 4). In turn, control of plasmin activity, as well as these other extracellular events, is principally mediated by plasminogen activators, which convert the inactive zymogen plasminogen to the active enzyme plasmin.

In clinical settings it is commonly desirable to activate or potentiate the fibrinolytic system. This is particularly necessary in cases of myocardial infarction in which coronary arteries become occluded and require recanalization. Catheterization has proven somewhat effective in such recanalization, but pharmacologic agents are desired to supplement or replace such invasive procedures to inhibit reocclusion. The study of the intricate system of thrombolysis and fibrinolysis has been a rapidly growing field, which has resulted in the development of a new generation of thrombolytic agents.

Previous therapeutic treatments for dissolving life-threatening clots have included injecting into the blood system various enzymes which are known to break down fibrin. The problems with these treatments is that the enzymes were not site-specific, and, therefore, would do more than just cause dissolution of the clot. In addition, these enzymes interfere with and destroy many vital protein interactions that serve to keep the body from bleeding excessively due to the many minor injuries it receives on a daily basis. Destruction of these safeguards by such enzymes can lead to serious hemorrhage and other potentially fatal complications.

Currently, the best known therapeutic agents for inducing or enhancing thrombolysis are compounds which cause the activation of plasminogen, the so-called "plasminogen activators" (Ref. 5) These compounds cause the hydrolysis of the arg560-val561 peptide bond in plasminogen. This hydrolysis yields the active two-chain serine protease, plasmin. A number of such plasminogen activators are known, including serine proteases such as urokinase plasminogen activator (u-PA), tissue-type plasminogen activator (t-PA), streptokinase (a non-enzyme protein) and staphylokinase. Of these, streptokinase is the most widely used therapeutic thrombolytic agent. However, while streptokinase and the other plasminogen activators have proven helpful in recanalization of coronary arteries, their ability to improve mortality is not devoid of side effects and their use still requires stringent control conditions to achieve success in a high percentage of cases (Ref. 6). In addition, the use of such compounds can cause bleeding complications in susceptible individuals. On the other hand, a drawback of the use of t-PA in clinical trials of human patients has been the rapid reformation of the clot after it has been dissolved, resulting in reocclusion.

Numerous studies have documented the ability of t-PA to initiate or potentiate thrombolytic phenomena (Ref. 7). As a result, t-PA, specifically its recombinant form, rt-PA, is becoming more popular as a thrombolytic pharmaceutical. Nonetheless, rt-PA does suffer from serious limitations, including extremely high dosage cost, and variable efficacy. In addition, specific rapid- acting inhibitors of t-PA have been identified in human plasma and other fluids (Ref. 8). A further approach to t-PA involves the potential use of gene transfer of and expression of recombinant t-PA in endothelial cells (Ref. 9). This procedure is exceedingly complex and is not likely to be practical as a thrombolytic treatment in the near future.

Exogenous enzymes are also known which degrade fibrin. Such enzymes include hemolytic enzymes collected from the venom of certain snakes, e.g., the families crotalidae and viperidae (Refs. 10–12). These enzymes have been identified as zinc metalloproteinases (Ref. 13). Fibrinolytic enzymes have also been obtained from leeches (Refs. 14–15), as well as from the growth medium of a bacterium which was recovered from leech intestinal tract (Ref. 16).

Endogenous matrix metalloproteinases (MMPs) or "matrixins" include three classes of enzymes: collagenases, gelatinases, and stromelysins. MMPs are known to have the capacity to degrade a number of proteins and proteoglycans which are associated with the extracellular matrix (ECM) of connective tissue. They have been shown to break down a number of proteins including collagen (I–IV, VII and X), laminin, fibronectin, elastin and proteoglycans. MMPs participate in the remodeling of tissues in physiological processes such as morphogenesis and embryonic development, as well as in the pathophysiology of wound healing, tumor invasion, and arthritis.

The regulation of MMPs and their inhibitors is under extensive and varied molecular and cellular control (Refs. 18–19). Known regulating factors include hormones, cytokines, proto-oncogenes, steroids, and growth factors. MMPs are blocked by specific inhibitors called "tissue inhibitors of metalloproteinases" (TIMPS) that can block the activity of each member of the family. An enzyme inhibitor complex is formed and no turnover of connective tissue takes place if the MMPs are present in excess. The main focus of research on ECM has been to limit ECM degradation by MMPs to interrupt or interfere with the progression of disease states. Several groups of investigators are making small molecules that could inhibit proteinases to alter their destructive activity in arthritis, and as antiangiogenic factors to inhibit tumor spread.

Matrix metalloproteinase 3 (MMP-3) belongs to the stromelysin class of matrix metalloproteinases. MMP-3 is expressed in mature macrophages, endothelial cells, smooth muscle cells and fibroblasts. The inactive zymogen, proMMP-3, is activated by neutrophil elastase, plasma kallikrein, plasmin, chymotrypsin, trypsin, cathepsin G, and mast cell tryptase, as well as by mercurial compounds (Refs. 20–21). Elevated levels of MMP-3 have been found in the joints of patients suffering from osteoarthritis and rheumatoid arthritis. Two very recent studies have shown the presence of matrix metalloproteinase 3 in atherosclerotic plaques (Refs. 22–23), but its function in this context has remained unelucidated. Indeed, MMP-3 has been viewed in these studies as a potential negative factor.

The known substrates of MMP-3 include proteoglycans, collagen type IV, fibronectin, and laminin. Such substrates are typical of matrix metalloproteinases in general (Ref. 24). There has been no suggestion, however, that any endogenous metalloproteinase might be involved in the degradation of fibrinogen or fibrin. Nor has there been any indication that metalloproteinases could be used for fibrinolysis or thrombolysis.

From the foregoing discussion, it becomes clear that significant gaps exist in the understanding of processes involved in thrombus formation and degradation. While certain approaches have been identified which permit a measure of control over these processes, these approaches suffer serious deficiencies related to cost, efficacy, or safety. The diagnosis and treatment of disease states associated with physiological processes involving fibrinogen and fibrin have also been found lacking.

As a result, there exists a need for effective compositions and methods for use in limiting thrombus development and inducing thrombolysis.

There is a need for methods of disrupting blood clots and atherosclerotic plaques, both in vitro, such as for diagnostic purposes, and in vivo, such as for therapeutic treatment of embolism, atherosclerosis and other clinically important disorders.

In addition, there exists a need for diagnostic and experimental materials and methods for revealing more information concerning the physical and chemical processes involved in thrombus formation and degradation.

Moreover, there is a need for effective treatment to restore at least some integrity to a damaged vessel wall, to promote regression of atherosclerotic plaques, and to aid in angioplasty and bypass surgery to prevent reocclusion.

SUMMARY OF THE INVENTION

The present invention provides a method for degrading fibrin, fibrinogen, and related substances (i.e., "fibrin (ogen)") by means of a fibrinolytic metalloproteinase (FMP). Preferably, the fibrinolytic metalloproteinase is endogenous, more preferably, a stromelysin. Most preferably, the fibrinolytic metalloproteinase includes matrix metalloproteinase-3 (MMP-3).

The inventive method may be performed in vitro. In vitro, the method involves contacting a tissue sample, such as blood or plasma, with at least one fibrinolytic matrix metalloproteinase. In this method, fibrin may be degraded as a constituent of clots and/or atherosclerotic plaques for purposes of investigating the structure of such materials, as well as for further investigation of the mechanisms of fibrinolysis and thrombolysis. Fibrinogen may be degraded for experimental or diagnostic purposes related to the formation of fibrin or to prevent potential growth of a fibrinogen-fibrin mesh.

In a preferred diagnostic method, the method includes contacting a sample containing fibrin(ogen) with at least one fibrinolytic metalloproteinase to provide degradation products. Preferably, the method includes analyzing the degradation products to characterize the fibrin(ogen). Such analysis typically includes differentially separating the various degradation products. The degradation products can be identified or measured by various means. For example, the fragments may be detected through antibodies which specifically bind to or associate with particular region(s) of fibrin(ogen), or fail to associate with them due to loss of epitope induced by enzymatic degradation. Preferably, such antibodies are monospecific, more preferably monoclonal. Synthetic and/or chimeric antibodies may be used, as may antigen binding regions such as Fab and F(ab')$_2$. Measurement of specific association between such antibodies and degradation fragments can provide qualitative, or quantitative information about the fibrin(ogen) sample being analyzed. Such antibodies may be detectably labeled to aid in the measurement of the types and amounts of the degradation products. Alternatively, antibodies fixed to a substrate may be employed to aid in the separation or purification of degradation fragments produced by a fibrinolytic metalloproteinase.

The invention also provides a method of performing thrombolytic, embolytic, or atherolytic therapy in a vertebrate subject, preferably a primate, more preferably a human. In this embodiment, the invention involves administering to a subject a therapeutically effective amount of at least one fibrinolytic matrix metalloproteinase. Typically, the fibrinolytic metalloproteinase is administered in a therapeutic composition comprising the metalloproteinase and a pharmacologically acceptable carrier or diluent. Optionally, the administered composition may further include one or more other active ingredients as an adjunct to the fibrinolytic activity of a metalloproteinase. Such adjunct compounds include, for example, plasminogen activators, hirudin, and/or anti-coagulants, such as heparin.

In addition, the invention provides diagnostic and therapeutic kits which include a fibrinolytic matrix metalloproteinase. The fibrinolytic metalloproteinase is preferably endogenous. Preferably, the metalloproteinase includes a stromelysin, more preferably MMP-3. Such kits may include one or more containers, as well as additional reagent(s)

and/or active and/or inert ingredient(s) for performing any variations on the inventive method. Exemplary reagents include, without limitation, synthetic substrates to test enzymatic activity, and antibodies (preferably monospecific, e.g., monoclonal) to measure increase or decrease of antigen level. Preferred kits include at least one therapeutically effective unit dose of a fibrinolytic metalloproteinase. Also preferred are kits which include means for administering, preferably parenterally, more preferably intravenously, a composition containing a fibrinolytic metalloproteinase. The kits may include more one or more other active ingredients as adjuncts such as plasminogen activators, hirudin, or anti-coagulants such as heparin. These other ingredients may be included in separate compositions in separate reagent containers or may be included with each other and/or the fibrinolytic metalloproteinase in a single reagent container. The kits may also include instructions for mixing or combining ingredients and or use of the kit according to the invention.

The invention further provides a method of controlling formation of thrombus caused by medical-related apparatus. In this embodiment, the method includes contacting a medical-related apparatus with a composition which includes a fibrinolytic matrix metalloproteinase, preferably MMP-3. The metalloproteinase desirably adheres or binds to a surface of the apparatus. The method may be used to modify blood-contacting surfaces of implantable prosthetic devices such as cannulae, catheters, grafts, stents, filters, coils, valves, and the like, to provide surfaces which inhibit the formation of clots or plaques. Alternatively, the method enables the fibrinolytic modification of apparatus such as blood collection tubes, culture flasks, test plates, pipets, reagent containers, tubing, membranes, and the like, to promote fibrinolysis and to inhibit the polymerization of fibrinogen and the formation of thrombus which might otherwise interfere with the experimental protocols. Likewise, the invention provides medical-related apparatus such as implantables, labware, and other devices for in vivo and in vitro uses, which apparatus has been modified to include adhered fibrinolytic metalloproteinase.

In still another embodiment, the invention provides a method of enhancing the regulation of fibrinolysis in a subject in need of such therapy. In this embodiment, the method of the invention includes inducing enhanced regulation of an endogenous fibrinolytic matrix metalloproteinase in a subject. Preferably, the method involves increasing the activity or expression of an endogenous fibrinolytic matrix metalloproteinase by treating the subject with somatic cell gene transfer therapy. Alternatively, the method involves decreasing the activity or expression of an endogenous fibrinolytic matrix metalloproteinase by treating the subject with somatic cell gene transfer therapy. Other therapeutic approaches may be employed which involve pharmaceutical compositions for either promoting or inhibiting the activity or the expression of an endogenous fibrinolytic matrix metalloproteinase.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein:

FIG. 2B is a graph illustrating comparative fibrin clot lysis by MMPs and plasmin as measured by the percentage of radioactivity in the residual clots.

DETAILED DESCRIPTION OF THE INVENTION

Figure 1:
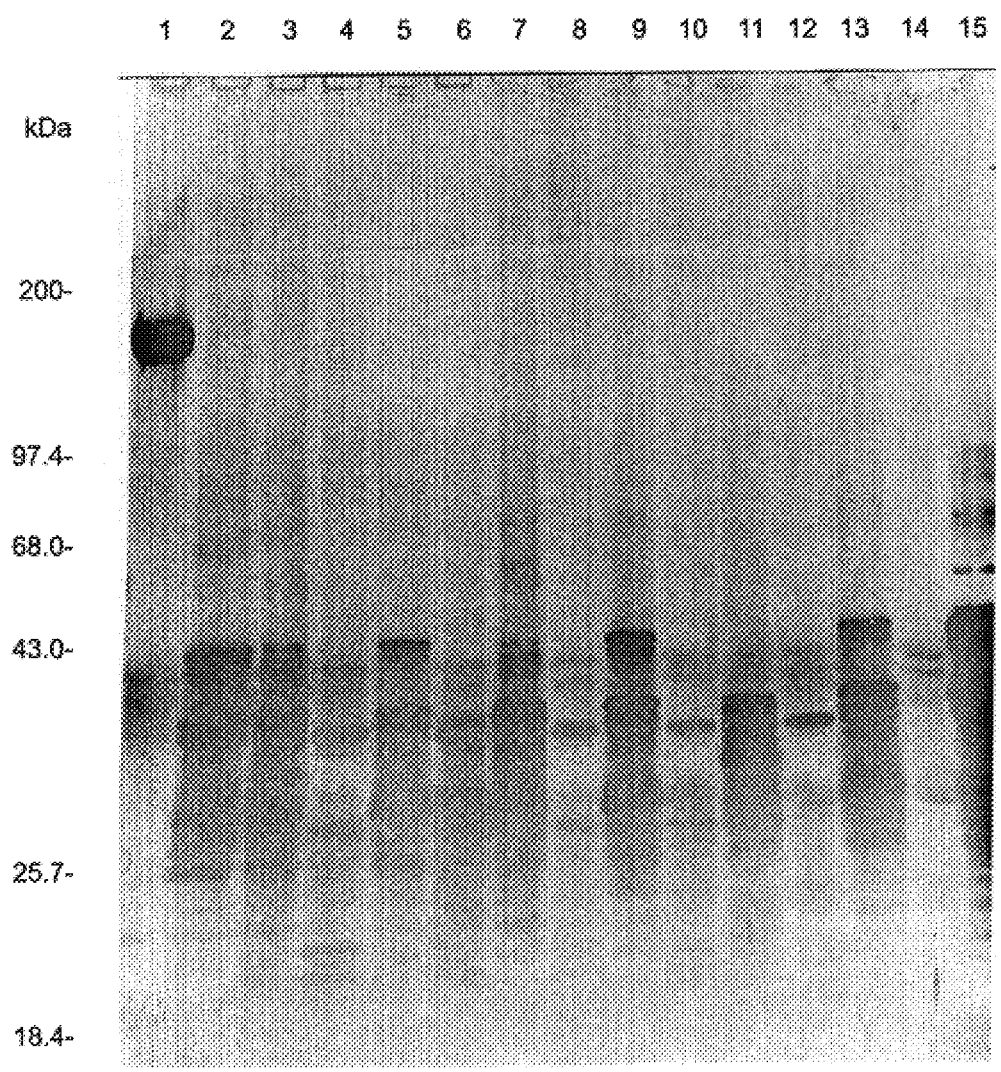
FIG. 1 shows an electrophoretic analysis of fibrinogen treated with MMP-1, MMP-2, and MMP-3, showing differential degradation of fibrinogen by each of the enzymes.

As noted above, two very recent studies have identified the presence of MMP-3 in atherosclerotic plaques (Refs. 22–23). These studies have regarded the presence of MMPs in the plaques as a negative factor which might favor fissure of the plaques. The present invention, however, is consistent with an entirely different understanding of the function of MMP-3. The invention relates to the unexpected role which MMP-3 has been discovered to play in the degradation of fibrinogen and fibrin.

For purposes of more clearly and accurately describing the invention herein, certain terminological conventions have been adopted in the following discussion. These conventions are intended to provide a practical means for enhancing description of the invention, but are not intended to be limiting, and the skilled artisan will appreciate that other and additional, albeit not inconsistent, interpretations may be implied.

For example, the invention relates to the use of a matrix metalloproteinase to degrade fibrin and fibrinogen. The matrix metalloproteinases useful according to the invention must exhibit some enzymatic activity against fibrin, fibrinogen, and or related proteins, polypeptides, or oligopeptides. Matrix metalloproteinases which exhibit this activity are termed "fibrinolytic matrix metalloproteinases" or "fibrinolytic MMPS".

The fibrinolytic matrix metalloproteinase may be exogenous or endogenous. It is preferred that the fibrinolytic metalloproteinase be endogenous. As used herein, the term "endogenous" means that the fibrinolytic metalloproteinase have an origin in the species in which the method of the invention is to be performed. The species may be any vertebrate, preferably a mammal, and more preferably a primate. Most preferably, the method is performed in a human subject. Accordingly, when the method of the invention is employed in a human subject, it is preferred that the active metalloproteinase be endogenous to humans, i.e., of human origin, whether employed as a pharmaceutical composition or resulting from therapy designed to improve the subject's internal control of his/her fibrinolytic system. For in vitro procedures, the origin of the fibrinolytic metalloproteinase is less critical, but it is preferred that the metalloproteinase have an origin as close as possible to the species origin of the biological sample being examined. In such methods, the metalloproteinase is endogenous to the sample if it is derived from the species to which the tested sample belongs.

Preferred endogenous fibrinolytic metalloproteinases include any of the stromelysin class of metalloproteinases. Preferred stromelysins include MMP-3 (stromelysin-1), MMP-10 (stromelysin-2), and MMP-11 (stromelysin-3). A highly preferred endogenous fibrinolytic MMP is MMP-3.

It is known that, due to the fluidity and complexity of the physiology of fibrin formation and degradation, many forms of fibrin and fibrinogen are present in the circulating blood as well as in thrombotic and atherosclerotic lesions. The many forms of these molecules result from continual assault by proteolytic enzymes which variously cleave the molecules. The method of the invention is performed by means of a fibrinolytic MMP which has activity against at least one fibrinogen- or fibrin-related compound. If a fibrinogen-derived molecule has previously been cleaved or modified to delete all MMP cleavage sites, then that molecule is no longer capable of acting as a substrate for a fibrinolytic MMP. Substrates for MMP-3 have now unexpectedly been found to include, inter alia, native fibrinogen and fibrin, and would also be expected to include modified, synthetic, and semisynthetic forms of these compounds, as well as a large number of cleavage products of these compounds. The class of substances which are derived from or related to fibrinogen and/or fibrin may be termed "fibrin(ogen)". The method of the invention may, therefore, be performed using any MMP which acts to degrade a fibrin(ogen) moiety. While such enzymes are generally termed "fibrinolytic", they may also be more precisely termed "fibrin(ogen)olytic" MMPs.

Fibrinogen (also abbreviated herein as "Fg") is known to be a homodimeric protein, in which each monomer includes three substantially homologous polypeptide chains, identified as the α (alpha), β (beta), and γ (gamma) chains. For a review see Doolittle (1987) (Ref. 24). Thus, fibrinogen has the structure $(\alpha\beta\gamma)_2$. All three fibrinogen subunits have coiled domains which permit the subunits to engage one another to form a "coiled coil" region in the fibrinogen monomer. In addition, the beta and gamma chains each have a globular domain, while the alpha chain is present in two forms; a predominant form having no corresponding globular domain ($\alpha$), and a less prevalent form in which a globular domain is present ($\alpha_E$) (Ref. 25). Accordingly, because fibrinogen is homodimeric and because two forms of the alpha subunit have been identified, two principal forms of fibrinogen are known: $(\alpha\beta\gamma)_2$ and $(\alpha_E\beta\gamma)_2$. Both forms of fibrinogen are considered to be substrates of fibrinolytic MMPs according to the invention. Artificial heterodimers of fibrinogen, as well as recombinant forms are also within the class of fibrinolytic MMP substrates.

As noted, fibrin (also abbreviated herein as "Fb") is generated through an induced and controlled polymerization of fibrinogen (Ref. 25). Given that various forms of fibrinogen are known in circulating blood, it is known that various polymerization structures for fibrin occur. Fibrin structure can affect the processes of fibrinolysis (Ref. 26). A fibrinolytic metalloproteinase has now been found to effectively lyse fibrin. It appears, therefore, that fibrinolytic metalloproteinases are active against fibrin without being substantially limited by peculiarities of fibrin cross-linking. Accordingly, fibrin is considered to be an MMP substrate according to the invention. Thus, fibrin which occurs naturally in a subject is suitable for degradation according to the invention, as is fibrin induced in vitro. Thus, clots which are induced in blood ex vivo, e.g., in a blood sample, may be degraded according to the invention. In such in vitro applications, a fibrinolytic metalloproteinase may be employed as a coating on a container such as blood collection tube. Also, artificial fibrin, formed from natural, synthetic, semisynthetic, recombinant and/or other types of fibrinogen may also be degraded by the method described herein.

Under physiologic conditions, plasmin is the central enzyme which acts to degrade fibrin. Plasmin action is restricted to the site of fibrin deposition by plasma control mechanisms that prevent proteolysis of circulating proteins. However, under pathologic conditions, plasmin is known to degrade plasma proteins, especially fibrinogen.

Degraded fibrinogen can be separated by ion-exchange chromatography into five fractions (A, B, C, D, and E), of which fragments D and E are the major end products of the original molecule. The identification and characterization of the transient intermediate fragments X and Y engendered the insight for the development of an asymmetric scheme of fibrinogen degradation (Ref. 1).

Classically, fibrinogen structure is bilaterally symmetrical, including a central globular domain E which is a "knot" made up of the N-terminal regions of all six chains in the fibrinogen molecule. From E extend two coiled coils each of which contains portions of one set of α, β, and γ chains. At the other ends of the coiled coils are globular domains D. Extending from the D domains, are the Aα chain extensions, which, in the $\alpha_E$ subunit only, terminate in another globular domain.

Under proteolytic attack by plasmin, initial cleavages liberate the carboxy-terminal, polar appendage of the Aα chain, and a peptide from the N-terminal portion of the Bβ chain (Bβ1–42). The remaining major fragment is Fragment X. Cleavages of all three polypeptide chains along one coiled coil connecting the central N-terminal knot (E) and a terminal (D) domain of fragment X split it asymmetrically. The result is one fragment D molecule, which consists of carboxy-terminal portions of the three chains, and a fragment Y moiety, consisting of central and terminal domains still connected by a coiled coil. Subsequent cleavage of the coiled coil of fragment Y produces a second fragment D and a fragment E moiety. Fragment X is slowly coagulable by thrombin, but fragments Y and D have potent antipolymerizing effects, due mostly to disruption of the proper alignment and continuation of build-up of the protofibrils of fibrin.

Knowledge of the conventional fragmentation of fibrinogen assists in providing a conceptual framework against which to compare the activity of other potential fibrinolytic enzymes. Moreover, antibodies have been developed which are specifically reactive with or specifically bind to only some of the fragments, thereby permitting molecular identification of fragments with great accuracy and precision (Ref. 27). Using this knowledge, fibrinolytic activity of an endogenous metalloproteinase has now been unexpectedly identified, thereby enabling the development of the method of the invention.

The invention provides, inter alia, a method of degrading fibrin(ogen). Generally, the method requires the use of an endogenous matrix metalloproteinase which possesses enzymatic activity against, i.e., can hydrolyze, fibrin and/or fibrinogen. The method includes contacting fibrin or fibrinogen with an effective amount of a fibrinolytic matrix metalloproteinase, preferably MMP-3.

The method typically involves contacting fibrinogen or fibrin with a matrix metalloproteinase. Compositions including a fibrinolytic metalloproteinase may also include other active and/or inert ingredients. Other active ingredients may include such ingredients as inhibitors of MMPs, plasminogen activators, other fibrinolytic enzymes, anti-coagulation reagents, etc. Should another active ingredient be employed, it is preferred to include in the composition a plasminogen activator. It has been found that matrix metalloproteinase 3, in particular, does not compete substantially with or substantially inhibit t-PA or plasmin. Accordingly, the method of the invention may include plasminogen activators such as u-PA, t-PA, staphylokinase, streptokinase or recombinant, synthetic, or semisynthetic forms thereof.

The invention also now permits the investigation of the interaction of MMP-3 with plasminogen activators, plasminogen activator inhibitors (e.g., PAI-1), and native plasminogen. For example, while it is known that plasmin can activate MMP-3, it is not known whether MMP-3 activates t-PA or u-PA, or if it might be activated by them instead. Nor is it known if MMP-3 might activate native plasminogen.

It may also be desirable to include an anticoagulation agent such as heparin, to inhibit or prevent re-coagulation. Such measures would be less critical in in vitro applications, but could be significantly helpful in in vivo applications. The combination of t-PA with heparin to define a dual-functional thrombolytic composition is illustrated in U.S. Pat. No. 5,130,143.

In one preferred embodiment, the method of the invention permits fibrinolytic therapy of a mammalian, preferably human, subject. In this embodiment, the method includes the administration to a subject of a therapeutically effective amount of a matrix metalloproteinase which degrades fibrin (ogen). The metalloproteinase preferably includes an endogenous metalloproteinase, more preferably a stromelysin, and most preferably MMP-3. The therapeutic method may be employed for thrombolysis, or for prevention of progression and facilitation of regression of atherosclerotic plaques. Thus, the method may be performed for acute or emergency therapy or for prolonged or chronic maintenance therapy to reduce the likelihood of or inhibit the development of abnormal thrombi, emboli or atherosclerotic plaques.

Modes of administration of such a composition are known in the art, and are related to those techniques employed in the administration of conventional thrombolytic agents. Such methods include, without limitation, parenteral methods, preferably intravascular methods such as intravenous injection, intraarterial injection, and administration by catheter.

The determination of the effective amount of a composition of the invention is within the discretion of the skilled clinician. Specific prophylactic or therapeutic dosages and the timing of administration can be selected depending upon prevailing conditions to achieve clinically acceptable treatment. The skilled clinician will take into account such factors as the age, sex, weight, and condition of the subject, as well as the route of administration. The skilled clinician will also recognize that the fibrinolytic activity of MMPs may be enhanced by the collateral administration (e.g. co-administration or sequential administration) of other active and/or inert substances. For example, it may be desirable to administer adjunct agents having activity in fibrinolysis. Such agents may have direct fibrinolytic activity or may be regulators or modulators of fibrinolysis in the system in which they are employed. For example, it may be preferred under certain clotting conditions, that other agents such as plasminogen activators, enzyme inhibitors, and/or anti-clotting factors be administered together with or ancillary to the administration of an MMP-containing composition. Thus, such other agent or agents may be included in the metalloproteinase-containing composition, or may be administered as part of another composition.

In another embodiment, the invention includes targeted fibrinolytic metalloproteinases, i.e., metalloproteinases which are bound to moieties having specificity for a biological target molecule. For example, a metalloproteinase may be bound to an antibody by methods known in the art for attaching proteins to antibodies. In this way a metalloproteinase may be preferentially directed to a fibrin(ogen) substrate for improving fibrin(ogen)olytic efficacy. Thus, a fibrinolytic metalloproteinase such as MMP-3 may be linked to antibodies having specificity for fibrin or a degradation product thereof, to platelets, specifically to P-selectin, to oxidized lipoproteins, etc.

The invention also provides a diagnostic method for the characterization of fibrinogen. In this method, fibrin(ogen) is contacted with an endogenous matrix metalloproteinase, preferably MMP-3, to produce degradation products. The degradation products are then analyzed to determine the types and amounts of cleavage products generated by the activity of the MMP.

Typically, the method involves the differential separation of degradation products, such as separation of the products by gel electrophoresis. The products are then measured such as by non-specific staining to reveal quantities of products of different sizes. Alternatively, the products can be identified by contacting the products with antibodies which are specifically reactive with or specifically associate with one or more domains of fibrin(ogen) (Ref. 27). Preferably, such antibodies are specifically reactive with a single degradation product, thereby permitting characterization of the product in relation to other products.

New antibodies, useful according to the diagnostic method of the invention, can be developed and detectably labeled with any detectable marker group. Suitable marker groups include, for example, fluorescent labels, enzyme labels, and radioactive labels. Detector groups useful according to the invention include, for example, fluorescein as a fluorescent label, horseradish peroxidase as an enzyme label, and Iodine-125 as a radioactive label. Additional fluorescent labels which can be utilized in the invention include, but are not limited to, rhodamine, phycoerythrin and additional compounds emitting fluorescent energy. Additional enzyme labels which can be utilized in this invention include, but are not limited to, glucose oxidase and alkaline phosphatase. Additional radioactive labels which can be utilized in this invention include, but are not limited to, Iodine-131 and Indium-111.

Suitable detectable labels may be selected from among those known in the art, such as radioactive labels, enzymes, specific binding pair components, colloidal dye substances, fluorochromes, reducing substances, latexes, digoxigenin, metals, particulates, dansyl lysine, antibodies, protein A, protein G, electron dense materials, chromophores, and the like. Effectively, any suitable label, whether directly or indirectly detectable, may be employed. One skilled in the art will clearly recognize that these labels set forth above are merely illustrative of the different labels that could be utilized in the diagnostic method of the invention.

Fibrinogen subunit-reactive antibodies can also be derivatized by conjugation to biotin, and used, upon addition of species of avidins which have been rendered detectable by conjugation to fluorescent labels, enzyme labels, radioactive labels, electron dense labels, etc., in a multiplicity of immunochemical and immunohistological applications.

Alternatively, the method of the invention may be performed using antibodies which have been attached or bound to substrates materials according to methods known to those skilled in the art. Such materials are generally substantially solid and relatively insoluble, imparting stability to physical and chemical disruption of the antibodies, and permitting the antibodies to be arranged in specific spatial distributions. Among substrate materials, materials may be chosen according to the artisan's desired ends, and include materials such as gels, hydrogels, resins, beads, nitrocellulose, nylon filters, microtiter plates, culture flasks, polymeric materials, and the like, without limitation.

The method of the present invention can involve immunological assays to determine the presence of fibrin(ogen) breakdown products in tissue samples from human or animal subjects. Biopsy and necropsy samples of subjects, as well as samples from tissue libraries or blood banks, can be evaluated for the presence of fibrin(ogen) MMP breakdown fragments using an anti-fibrinogen antibodies. Moreover, suitable preparations may be devised for in vivo use, such as for the visualization of fibrinogen or fibrinogen-containing substances and structures in a living subject. In this way the progression of fibrinolysis induced by MMPs can be assessed in situ.

In one such embodiment, an endogenous fibrinolytic MMP, preferably MMP-3, is bound to a substrate material such as a membrane, blood collection tube, microtiter plate, culture flask, or the like. In this manner, the method of the invention may be performed in the absence of soluble MMP, to induce fibrin(ogen)olysis in a fluid sample. Alternatively, this approach is useful in coating membranes and prosthetic devices.

Indeed, in another embodiment, the invention provides a method of controlling formation of clots or plaques caused or induced by medical-related apparatus. In this embodiment, the method includes contacting a medical-related apparatus with a composition which includes a fibrinolytic matrix metalloproteinase, preferably MMP-3. This method may be used to cause a metalloproteinase to bind or adhere to a surface. It is believed that any apparatus which would contact blood can be so modified by methods known in the art which permit the attachment of proteins to substrate materials. For example, the method may be used to modify blood-contacting surfaces of implantable prosthetic devices such as cannulae, catheters, grafts, stents, filters, coils, valves, and the like, to provide surfaces which inhibit the formation of thrombus. Alternatively, the method enables the fibrinolytic modification of apparatus such as blood collection tubes, culture flasks, test plates, pipets, reagent containers, tubing, membranes, and the like, to promote fibrinolysis and to inhibit the formation of thrombus which might otherwise interfere with the experimental protocols. Likewise, the invention provides medical-related apparatus such as implantables, labware, and other devices for in vivo and in vitro uses which possess the capacity or inhibiting thrombus formation by promoting the degradation of fibrin(ogen). The metalloproteinase may be adhered to an apparatus either permanently or reversibly, such as for delivery of metalloproteinase from an apparatus into solution.

The invention also provides a method of enhancing regulation of fibrinolysis in a subject in need of such therapy. In this embodiment, the method of the invention includes inducing enhanced regulation of an endogenous fibrinolytic matrix metalloproteinase in a subject. Preferably, the method involves increasing or decreasing the activity or expression of an endogenous fibrinolytic matrix metalloproteinase by treating the subject with somatic cell gene transfer therapy. Any gene therapy approach may be employed according to this embodiment. Thus, up-regulation of MMP expression may be accomplished by introducing a gene for a fibrinolytic MMP by ex vivo or in vivo gene transfer techniques. Alternatively, up-regulation of an MMP may be accomplished by inhibiting the expression of an MMP inhibitor via anti-sense technology. Down-regulation of MMP activity may be accomplished by these techniques, the design and implementation of which are within the skill of those in the art. A brief overview of several gene therapy methods is provided in Glick et al., which is incorporated herein by reference (Ref. 28). Other therapeutic approaches may be employed which involve pharmaceutical compositions for either promoting or inhibiting the activity or the expression of an endogenous fibrinolytic matrix metalloproteinase. Given the complexity of the fibrinolytic regulation system, and given the unexpected role of MMPs in that regulatory scheme, it would appear to those skilled in the art that many potential avenues exist for adjustment of the fibrinolytic regulatory status of a subject.

The following examples are intended to assist in a further understanding of the invention. The particular materials and conditions employed are intended to be further illustrative of the invention and are not limiting upon the reasonable scope thereof.

EXAMPLE 1

Fibrinogen Degradation Experiments

MMP-1 (interstitial collagenase), MMP-2 (72 kD gelatinase) and MMP-3 (stromelysin) were prepared according to the methods described by Nagase et al. (Refs. 13, 20–21) and the documents cited therein. Fibrinogen and fibronectin were prepared in accordance with the method of Bini et al. (Ref. 29) and the documents cited therein. The disclosure of the Bini et al. publication is incorporated herein by reference. The MMPs were separately incubated with fibrinogen or fibronectin in various amounts and for various time intervals. Fibronectin (15 $\mu$g) or fibrinogen (15 $\mu$g) were incubated with MMP-1 (0.6 $\mu$g), MMP-2 (0.6 $\mu$g), or MMP-3 (0.6 μg or 6 μg) at 37° C. for 2, 6, and 24 hours, respectively (Enzyme:Subtrate ratio (E:S)=1:20 for each enzyme, and E:S=1:3.3 for MMP-3). The reactions were terminated by adjusting the digest mixture to 25 mM EDTA.

Following reaction, each of the reaction products was mixed with reducing or non-reducing sodium dodecyl sulfate (SDS) gel buffer, and subjected to 5–15% sodium dodecyl sulfate-polyacrylamide gel electrophoresis (SDS-PAGE). The pattern of degradation of fibronectin by each of the MMPs was consistent with previous studies (Ref. 30), thus serving as a control parameter against which to evaluate the activity of the enzymes against fibrinogen.

FIG. 1 illustrates the degradative effects upon fibrinogen by each of the three tested enzymes. The samples shown in FIG. 1 are as follows:

| Lane No. | Sample |
|---|---|
| 1 | Fibronectin |
| 2 | Fibrinogen |
| 3 | Fibrinogen with MMP-1 (1:20) for 120' |
| 4 | Fibrinogen with MMP-2 (1:20) for 120' |
| 5 | Fibrinogen with MMP-3 (1:20) for 120' |
| 6 | Fibrinogen with MMP-3 (1:3.3) for 120' |
| 7 | Fibrinogen with MMP-1 (1:20) for 360' |
| 8 | Fibrinogen with MMP-2 (1:20) for 360' |
| 9 | Fibrinogen with MMP-3 (1:20) for 360' |
| 10 | Fibrinogen with MMP-3 (1:3.3) for 360' |
| 11 | Fibrinogen with MMP-1 (1:20) for 24 hrs |
| 12 | Fibrinogen with MMP-2 (1:20) for 24 hrs |
| 13 | Fibrinogen with MMP-3 (1:20) for 24 hrs |
| 14 | Fibrinogen with MMP-3 (1:3.3) for 24 hrs |
| 15 | Fibrinogen |
| 16 | BRL |

The degradation of fibrinogen by the three MMPs was as follows:

Fibronectin control with no enzyme showed no degradation (lane 1);

Fibrinogen control with no enzyme showed no degradation (lanes 2 and 15);

MMP-1 had some effect on the degradation of the α chain at 24 hours (lane 11), but little effect at 2 hours (lane 3) or 6 hours (lane 7);

MMP-2 had some effect on both the α and γ chains within 2 hours after the start of incubation (lane 4), but the apparent digestion showed no progression from 6 to 24 hours (lanes 8, 12); and MMP-3 affected all three fibrinogen chains (α, β, and γ), and the extent of digestion increased progressively with time (lanes 5–6, 9–10, and 13–14).

This example shows clearly that MMP-3 has a distinct capacity to degrade fibrinogen, which distinguishes MMP-3 from the other MMPs tested in this procedure.

EXAMPLE 2

Mixtures of enzyme/fibrinogen preparations (identical to those obtained in Example 1) were incubated for 1.5 and 3 hours, and clotting times of the digested fibrinogen were compared with those of plasmin/fibrinogen digests incubated for the same times. Comparable clotting assays of enzyme/fibrinogen preparations identical to those obtained in Example 1 were incubated for 24 hours were compared to plasmin digests of fibrinogen after incubation for 24 hours. Comparable enzyme:substrate ratios were employed for each enzyme. Results showed that for a given enzyme:substrate ratio, fibrinogen exposed to MMP-2 was still clottable, while both plasmin and MMP-3 digests of fibrinogen were non clottable. High performance liquid chromatography (HPLC) analysis of the supernatants of the digests of fibrinogen showed normal release of fibrinopeptides A and B. These results are tabulated in Table I, below.

TABLE I

Thrombin Clotting Times

| Sample | E:S w/w | Concentration μg | Incubation time (hrs) | Thrombin time | Turbidity (same day) | Turbidity (next day) |
|---|---|---|---|---|---|---|
| Fg control (untreated) (120 μg) | — | — | — | 68" | 0.841 | 0.973 (n = 5) |
| MMP-2 | 1:600 | 0.2 | 1.5 | >15 min | — | 0.022 |
|  |  |  | " | unclottable | — | 0.022 |
|  |  |  | 3 | soft clot | — | 0.103 |
|  |  |  | " | next day | — | — |
| " | 1:200 | 0.6 | 1.5 | >10 min | 0.433 | 0.963 |
|  |  |  | " | 12'01 | 0.377 | 0.823 |
|  |  |  | 3 | >1 min | 0.681 | 1.039 |
|  |  |  | " | >1 min | 0.758 | 1.125 |
| MMP-3 | 1:600 | 0.2 | 1.5 | >10 min | — | 0.025 |
|  |  |  | " | unclottable | — | 0.035 |
|  |  |  | 3 | soft clot | — | 0.004 |
|  |  |  | " | the next day | — | 0.029 |
| " | 1:200 | 0.6 | 1.5 | >10 min | — | 0.001 |
|  |  |  | " | unclottable | — | 0 |
|  |  |  | 3 | no clot | — | 0.008 |
|  |  |  | " | the next day | — | 0.012 |
| Plasmin | 1:1200 | 0.1 | 1.5 | 107.5" | 0.396 | all |
|  |  |  | " | 103.9" | 0.399 | clots |
|  |  |  | 3 | 60.9" ? | 0.486 | digested |
|  |  |  | " | 139.1" | 0.502 | O.N. |
| " | 1:240 | 0.5 | 1.5 | unclottable | — | — |
|  |  |  | " | " | — | — |
|  |  |  | 3 | " | — | — |
|  |  |  | " | " | — | — |

EXAMPLE 3

Fibrin clots were made from purified fibrinogen according to the method of Bini et al. (Ref. 29) and the references cited therein. $^{125}$I-Fg prepared according to known methods was added before clotting. The clots were incubated with MMP-2, MMP-3, and plasmin in comparable enzyme:substrate ratios at different time intervals. Clots were made with 120 μg fibrinogen and degraded with 0.6 μg or 6 μg of MMPs, corresponding to 1:20 and 1:200 E:S ratios, respectively, or with 0.1 μg or 0.5 μg of plasmin, corresponding to 1:240 and 1:1200 E:S ratios, respectively. Clots were separated from the supernatants by centrifuging at 13,000 rpm for 20 minutes in a Sorvall RCL-B centrifuge (SS-34 rotor) from Sorvall DuPont Instruments. Samples were counted in a Packard Auto-γ-5000 Series gamma counter.

Figure 2A:
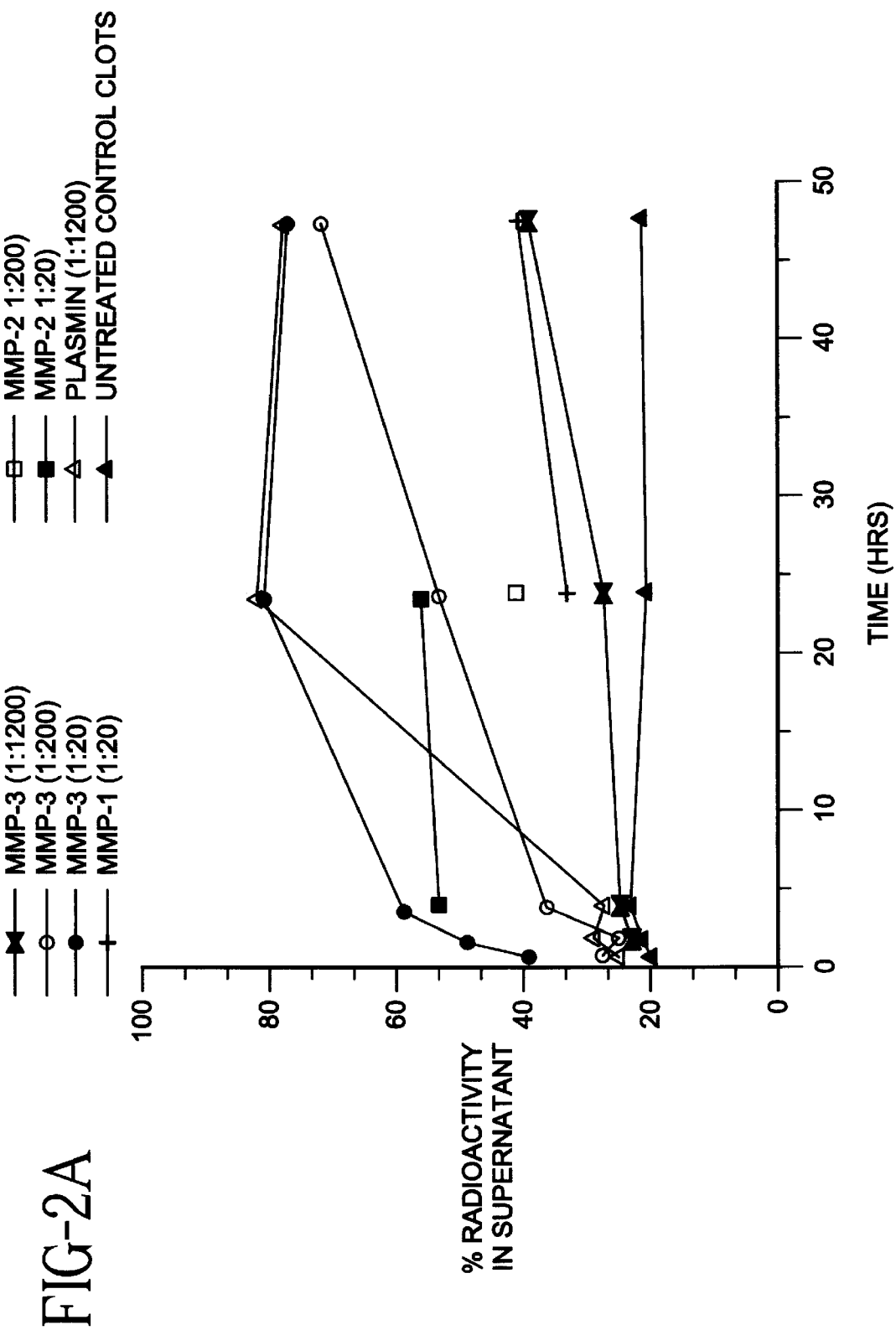
FIG. 2A is a graph illustrating comparative fibrin clot lysis by MMPs and plasmin as measured by the percentage of radioactivity in the sample supernatants.

The results of this experiment are presented in FIGS. 2A and 2B, which show the percent radioactivity in the supernatants (FIG. 2A) and in the residual clots (FIG. 2B). After 24 hours of incubation, both the MMP-3 and plasmin samples showed release of over 80% of the radioactivity into the supernatants (average of three experiments) (FIG. 2A). Residual activity in the clots was less than 10% (FIG. 2B), and the clots appeared dissolved by both MMP-3 and plasmin. See FIGS. 2A and 2B. Digestion of fibrin clots with MMP-2 for comparable enzyme:substrate ratios released less than 60% of radioactivity at 24 hours (FIG. 2A). Residual activity in the clot was 40% and 35% at 4 and 24 hours, respectively (FIG. 2B). Incubation with a mixture of MMP-3 and plasmin in the sample produced results similar to those produced by either enzyme alone. This indicates that the two enzymes do not interfere with one another. Identical experiments were performed using clots made from plasma, and the same results were obtained (data not shown).

EXAMPLE 4

Samples from fibrin degradation experiments without radiolabeled fibrinogen were subjected to SDS-PAGE using both reducing and non-reducing conditions. Samples were resolved via PAGE (5–15% gradient or 5–7% mini-gels) following generally accepted procedures (Refs. 31–32). Following electrophoresis, resolved proteins were transferred to nitrocellulose. Protein was stained with colloidal gold on the nitrocellulose membrane. The patterns of dose-dependent and time-dependent degradation of fibrinogen and fibrin by MMP-2, MMP-3 and plasmin are shown in FIGS. 3A–3C.

Figure 3A:
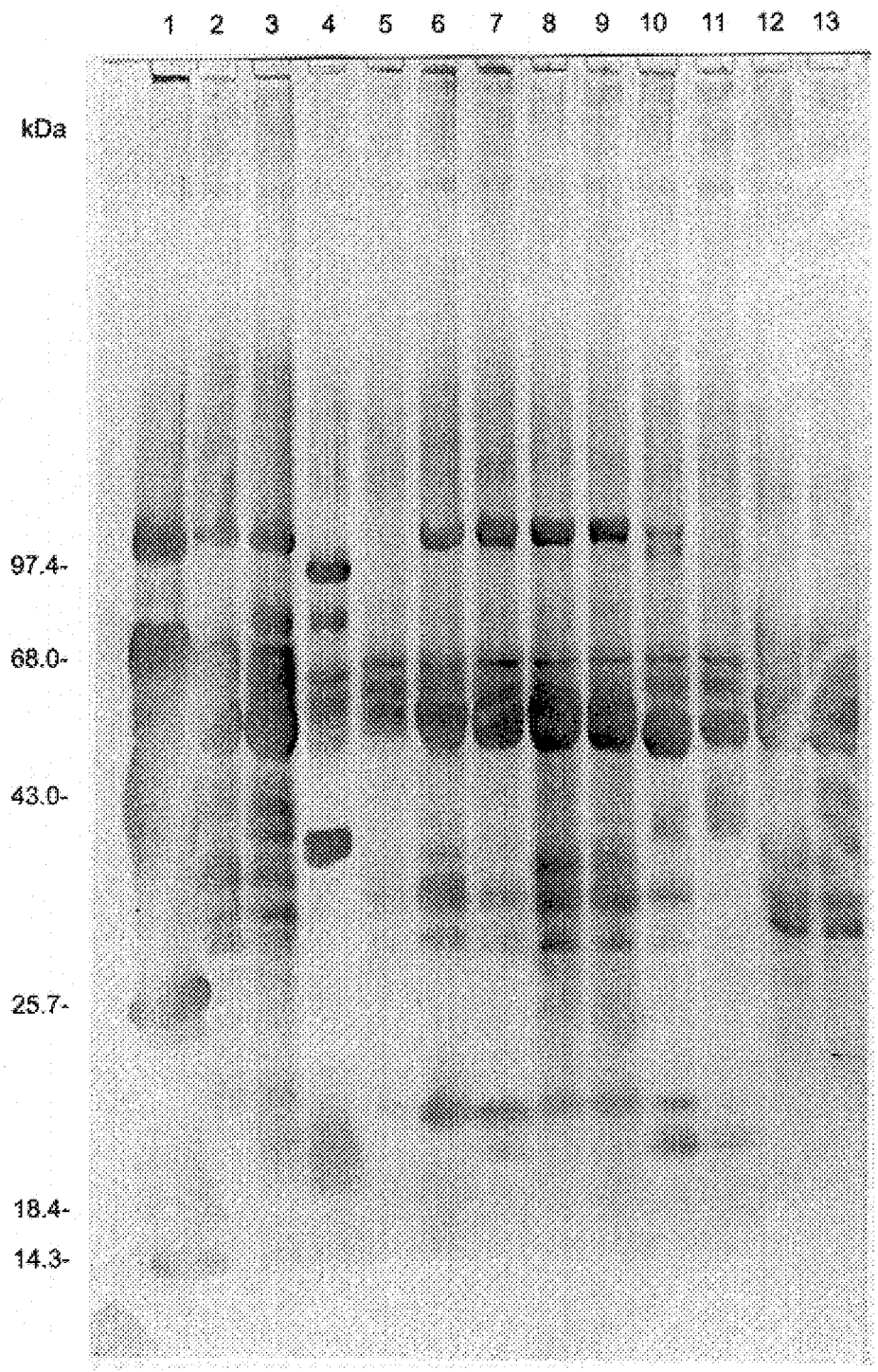
FIG. 3A shows an electrophoretic analysis of fibrin treated with MMP-2, MMP-3, and plasmin, showing differential degradation of fibrinogen by each of the enzymes.
Figure 3B:
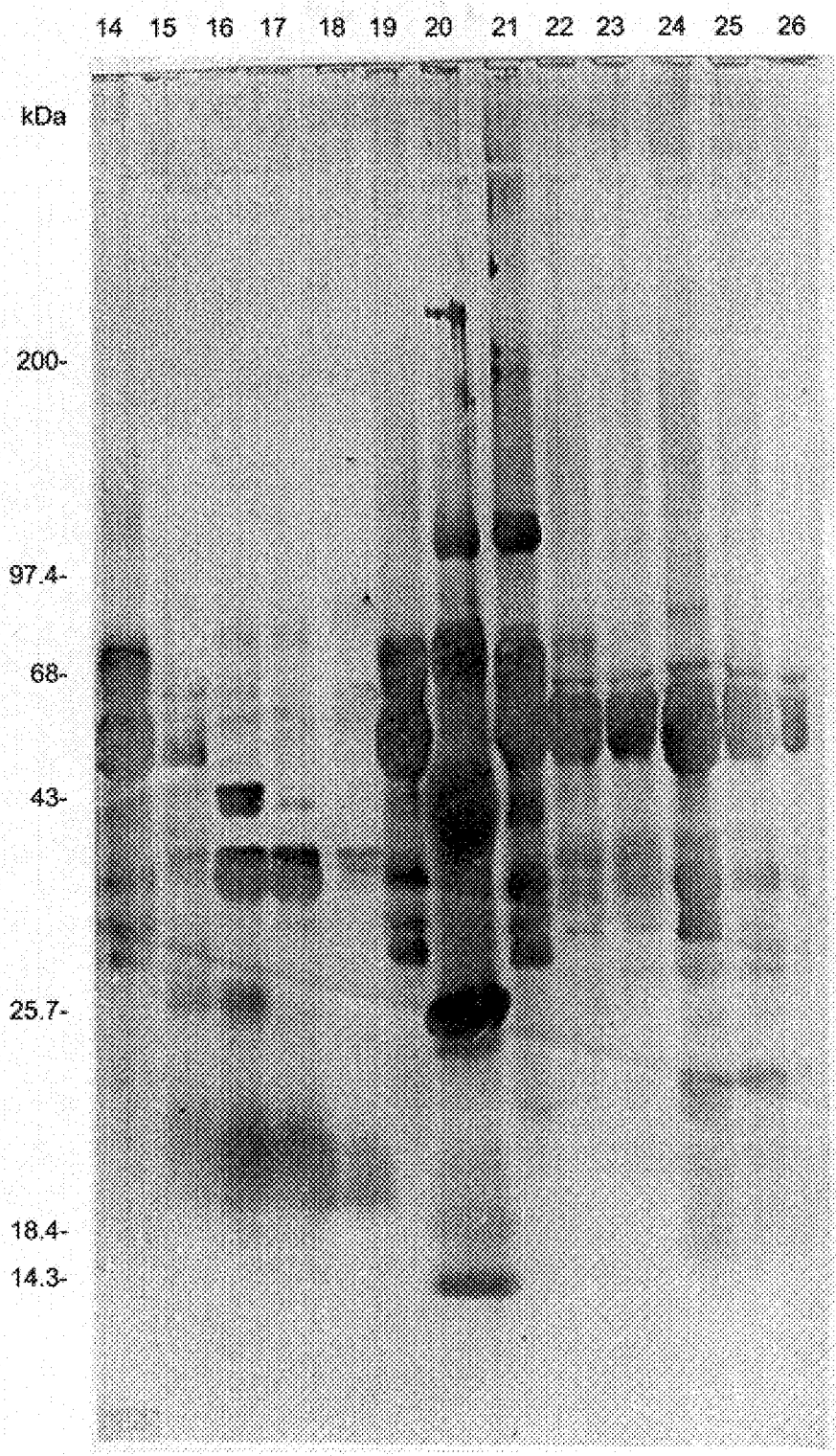
FIG. 3B shows an electrophoretic analysis of fibrinogen treated with plasmin and MMP-2, showing differential degradation of fibrinogen by the two enzymes.
Figure 3C:
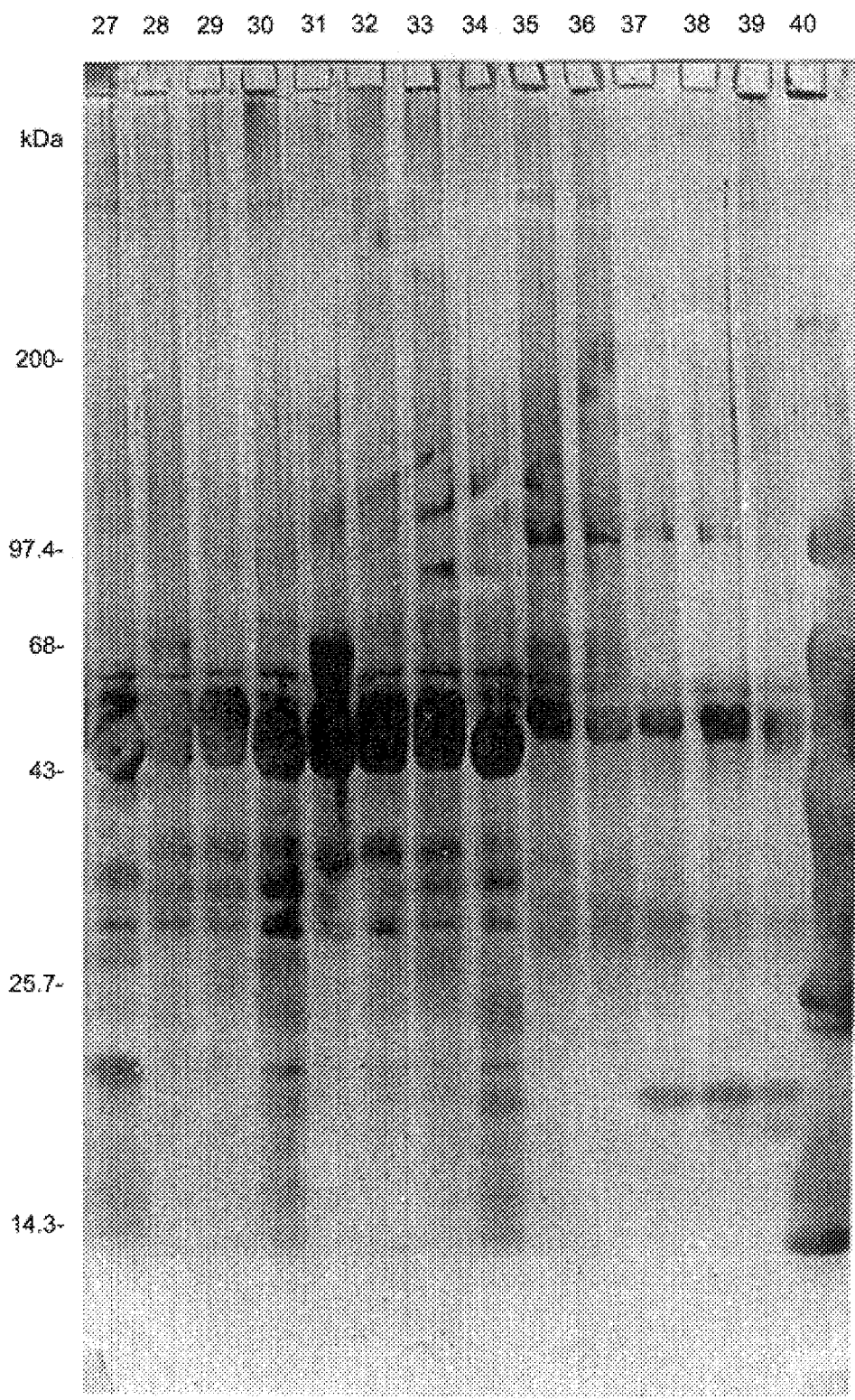
FIG. 3C shows an electrophoretic analysis of fibrinogen treated with MMP-3 and fibrin treated with MMP-2, showing time-dependent degradation of the substrates by each of the enzymes.

FIG. 3A shows degradation of fibrin γ dimer (96 kDa) in lane 10 (6 μg MMP-3) and complete degradation in lane 11 (12 μg MMP-3). Treatment with MMP-2 (lanes 5–7), by contrast, did not show any degradation of fibrin γ dimer, indicating that cross-linked fibrin is not degraded by MMP-2. Also, the pattern of degradation by MMP-3 is different from the pattern of plasmin degradation of fibrin. In fact, plasmin decreases the molecular weight of the γ dimer, but does not monomerize it (lane 3, 4) even at higher E:S ratio (1:24).

The key to FIG. 3A is as follows:

| Lane No. | Sample |
|---|---|
| 1 | BRL |
| 2 | Fibrin |
| 3 | Fibrin degraded with plasmin (1:1200) for 24 hrs |
| 4 | Fibrin degraded with plasmin (1:240) for 24 hrs |
| 5 | Fibrin degraded with MMP-2 (1:600) for 24 hrs |
| 6 | Fibrin degraded with MMP-2 (1:200) for 24 hrs |
| 7 | Fibrin degraded with MMP-2 (1:20) for 24 hrs |
| 8 | Fibrin degraded with MMP-3 (1:600) for 24 hrs |
| 9 | Fibrin degraded with MMP-3 (1:200) for 24 hrs |
| 10 | Fibrin degraded with MMP-3 (1:20) for 24 hrs |
| 11 | Fibrin degraded with MMP-1 (1:10) for 24 hrs |
| 12 | Fibrinogen |
| 13 | BRL |

In FIGS. 3B and 3C, progressive degradation of fibrinogen by each of plasmin, MMP-2, and MMP-3 is shown. Both MMP-2 and MMP-3 have a fibrinogen degradation pattern which is different from that of plasmin. Both show similar degradation of the α chain (FIG. 3B, lanes 22–26, and FIG. 3C, lanes 28–30). In addition, degradation of the γ-chain by each of MMP-2 and MMP-3 results in different and characteristic lower molecular weight fragments.

The key to FIG. 3B is as follows:

| Lane No. | Sample |
|---|---|
| 14 | Fibrin degraded with Plasmin (1:1200) for 3 hrs |
| 15 | Fibrin degraded with Plasmin (1:1200) for 24 hrs |
| 16 | Fibrin degraded with Plasmin (1:240) for 1 hr |
| 17 | Fibrin degraded with Plasmin (1:240) for 3 hrs |
| 18 | Fibrin degraded with Plasmin (1:240) for 24 hrs |
| 19 | BRL |
| 20 | Fibrinogen |
| 21 | Fibrin |
| 22 | Fibrin degraded with MMP-2 (1:600) for 1 hr |
| 23 | Fibrin degraded with MMP-2 (1:600) for 3 hrs |
| 24 | Fibrin degraded with MMP-2 (1:600) for 24 hrs |
| 25 | Fibrin degraded with MMP-2 (1:200) for 1 hr |
| 26 | Fibrinogen degraded with MMP-2 (1:200) for 3 hrs |

The key to FIG. 3C is as follows:

| Lane No. | Sample |
|---|---|
| 27 | Fibrin degraded with MMP-2 (1:200) for 24 hrs |
| 28 | Fibrinogen degraded with MMP-3 (1:600) for 1 hr |
| 29 | Fibrinogen degraded with MMP-2 (1:600) for 3 hrs |
| 30 | Fibrinogen degraded with MMP-2 (1:600) for 24 hrs |
| 31 | Fibrinogen |
| 32 | Fibrinogen degraded with MMP-3 (1:200) for 1 hr |
| 33 | Fibrinogen degraded with MMP-2 (1:200) for 3 hrs |
| 34 | Fibrinogen degraded with MMP-2 (1:200) for 24 hrs |
| 35 | Fibrin |
| 36 | Fibrin |
| 37 | Fibrin degraded with MMP-2 (1:200) for 24 hrs |
| 38 | Fibrinogen degraded with MMP-2 (1:20) for 24 hrs |
| 39 | Fibrin degraded with MMP-3 (1:200) for 24 hrs |
| 40 | BRL |

EXAMPLE 5

Immunoblots performed using standard techniques were performed on metalloproteinase digests of fibrin with a panel of monoclonal antibodies (MoAbs) (see Table II) to identify how the three chains of fibrin are cleaved by MMP-3 in comparison with plasmin. Monoclonal antibodies were prepared according to techniques known in the art.

TABLE II

MONOCLONAL ANTIBODIES

| Antibody | Isotype | Cross-Reacts With |
|---|---|---|
| MOAb/Fd4-7B3 | IgG1,k | fibrinogen, fragments D/D-dimer |
| 1747 | polyconal | fibrinogen, fragments D/D-dimer |
| MoAb/GC4 | IgG1,k | fragments D/D-dimer, not fibrinogen |
| MoAb/2N3H10 | IgG1,k | fibrinogen, fibrin and plasmin-derived fragment E from both |
| MoAb/4A5 (Gift) | IgG1,k | γ 397–311, fibrinogen and fragments D/D-dimer |
| MoAb/1D4 | IgG1,k | Aα 349–406, fibrinogen, fibrin and plasmin digests of both |
| MoAb/1C2-2 | IgG1,k | Aα 529–539, fibrinogen, fibrin and plasmin digests of both |
| MoAb/1-8C6 | IgG2a,k | Bβ 1–42, fibrinogen/fibrin I, not fibrin II |
| MoAb/T2G1 | IgG1,k | Bβ 15–42, fibrin II, not fibrinogen/fibrin I |
| MoAb/1C5 | IgG2a,k | γ1–78, not fibrinogen |
| MoAb/44-3 | IgG1,k | γ95–265, Ho-1-DSK, not fibrinogen |
| MoAb/4-2 | IgG1,k | γ392-406, fibrinogen and fragments D/D-dimer only after denaturation |

Nitrocellulose membranes of 5% non-reduced and 7% reduced mini-gels (phosphate system) were incubated with selected antibodies. Bound peroxidase complexes were detected using the chemiluminescent substrate luminol (ECL Western blotting detection system, Amersham LIFE SCIENCE, Arlington Hts., Ill.). Light emitted from the hydrolysis of the added luminol substrate exposed the provided x-ray film in 10 to 30 seconds (Kodak χ-Omat RP.) The results are illustrated in FIGS. 4–6.

Figure 4A:
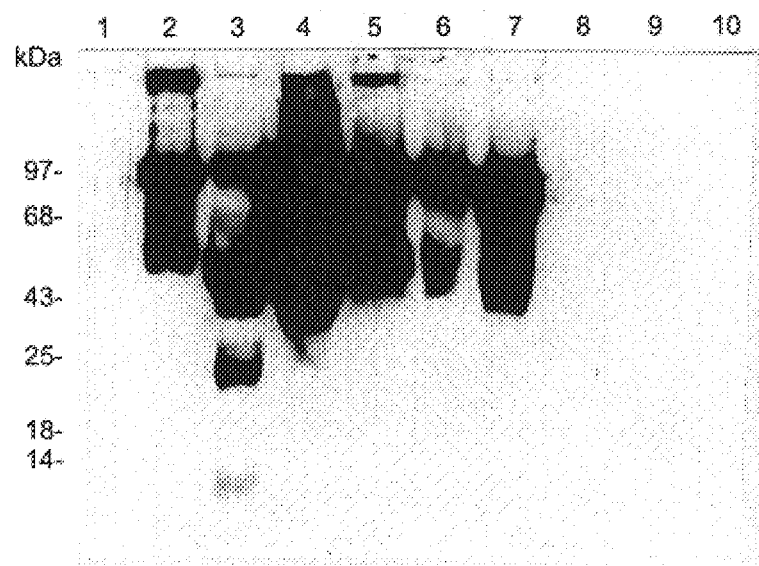
FIG. 4A shows an immunoblot of the degradation products of fibrin digestion by MMP-3 and plasmin, as measured with MoAb/4A5 ($\gamma$ 397–411).
Figure 4B:
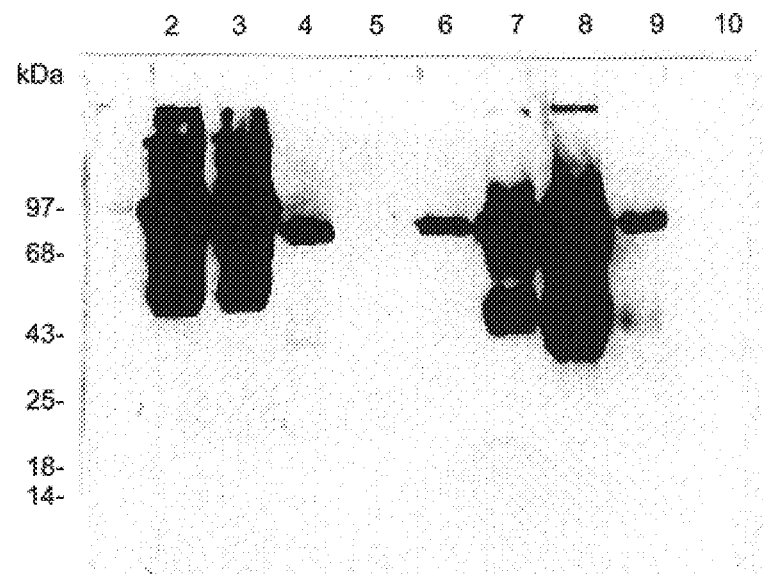
FIG. 4B shows an immunoblot of the degradation products of fibrin digestion by MMP-3 and plasmin, as measured with MoAb/4A5 ($\gamma$ 397–411).

FIGS. 4A and 4B show immunoblots of the degradation products of fibrin digestion by MMP-3 and plasmin. The key to FIG. 4A is as follows:

| Lane No. | Sample |
|---|---|
| 1 | BRL |
| 2 | Fibrin clot 4 hr |
| 3 | Fibrinogen |
| 4 | Fibrin Plasmin digest |
| 5 | Fibrin MMP-3 (0.6 μg) 24 hr prec |
| 6 | Fibrin MMP-3 (0.6 μg) 24 hr super |
| 7 | Fibrin MMP-3 (6 μg) 4 hr whole |
| 8 | Fibrin MMP-3 (6 μg) 48 hr whole TNE |
| 9 | Fibrin MMP-3 (6 μg) 48 hr whole |
| 10 | BRL |

The key to FIG. 4B is as follows:

| Lane No. | Sample |
|---|---|
| 1 | BRL |
| 2 | Fibrin clot 24 hr |
| 3 | Fibrin clot 48 hr |
| 4 | Fibrin MMP-3 (6 μg) 24 hr prec |
| 5 | Fibrin MMP-3 (6 μg) 24 hr super |
| 6 | Fibrin MMP-3 (6 μg) 24 hr mixture of above |
| 7 | Fibrin Plasmin (0.03 μg) 24 hr whole |
| 8 | Fibrin Plasmin (0.03 μg)/MMP-3 (0.6 μg) 24 hr prec |
| 9 | Fibrin Plasmin (0.03 μg)/MMP-3 (0.6 μg) 24 hr super |
| 10 | BRL |

The antibody used for the blots shown in FIGS. 4A and 4B was MoAb/4A5, which is specific for the cross-linking region of the gamma chain of fibrinogen (γ 397–411). It is evident that at 24 hours MMP-3 (0.6 μg) has initiated degradation of the γ—γ region (FIG. 4A, lanes 5 and 6). MMP-3 at ten-fold greater concentration (6 μg (E:S=1:20)) shows a similar pattern of degradation at 4 hours (FIG. 4A, lane 7). MMP-3 (6 μg) at 24 hours shows degradation of the γ—γ region (FIG. 4B, lanes 4 and 6). Immunoreactivity of the cleaved fragments is not recovered in the supernatants (FIG. 4B, lane 5). At 48 hours immunoreactivity of the γ 397–411 epitope is lost (FIG. 4A, lanes 8, 9). This indicates that cleavage has occurred in the region of this epitope. Immunoblot of the same samples under non-reducing conditions also showed loss of immunoreactivity upon monomerization of the γ dimer.

Figure 5A:
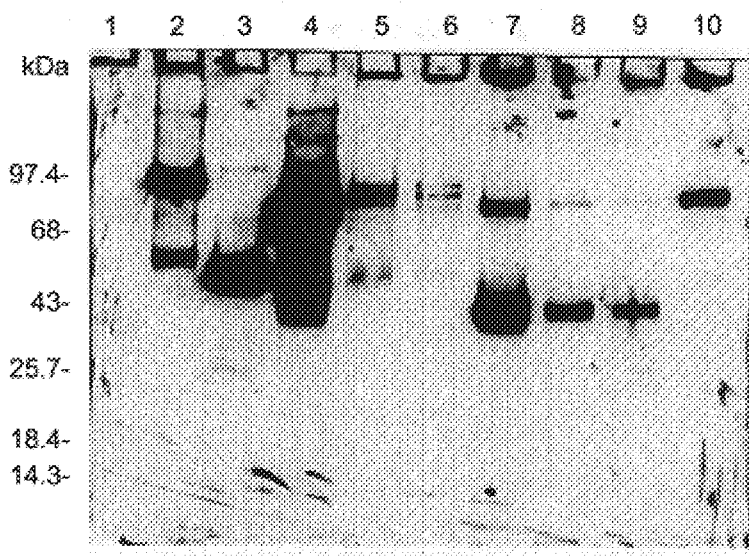
FIG. 5A shows an immunoblot of the degradation products of fibrin digestion by MMP-3 and plasmin, as measured with MoAb/4-2 ($\gamma$ 392–406), under reducing conditions.
Figure 5B:
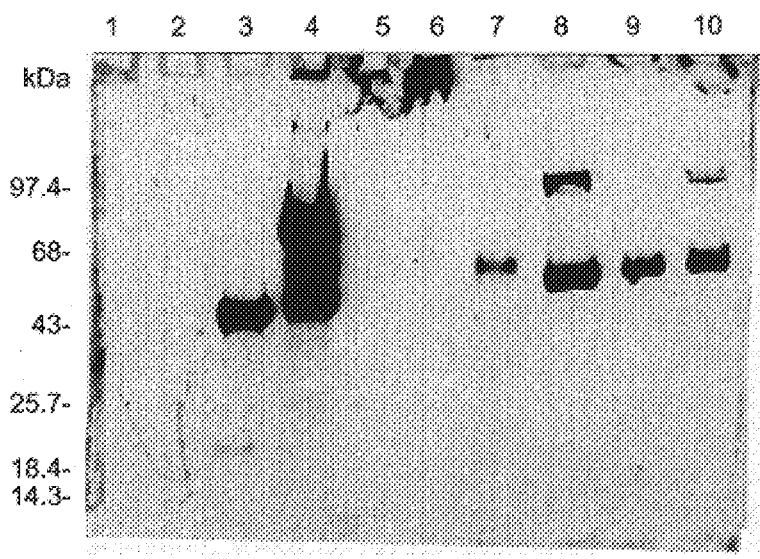
FIG. 5B shows an immunoblot of the degradation products of fibrin digestion by MMP-3 and plasmin, as measured with MoAb/4-2 ($\gamma$ 392–406) under non-reducing conditions.

FIGS. 5A and 5B show immunoblots of the degradation products of fibrin digestion by MMP-3 and plasmin with MoAb/4-2. This antibody is specific to an epitope located terminally to the one reactive with 4A5, i.e., γ 392–406. This antibody reacts with fibrinogen and the D and D-dimer fragments only after denaturation. The digests were examined under reducing and non-reducing conditions (FIGS. 5A and 5B, respectively). The key to FIG. 5A is as follows:

| Lane No. | Sample |
|---|---|
| 1 | BRL |
| 2 | Fibrin clot 24 hr |
| 3 | Fibrinogen |
| 4 | Fibrin Plasmin digest |
| 5 | Fibrin MMP-3 (0.6 μg) 24 hr prec |
| 6 | Fibrin MMP-3 (0.6 μg) 24 hr. super |
| 7 | Fibrin MMP-3 (6 μg) 24 hr prec |
| 8 | Fibrin MMP-3 (6 μg) 48 hr whole TNE |
| 9 | Fibrin MMP-3 (6 μg) 48 hr whole |
| 10 | Fibrin Plasmin (0.03 μg) 24 hr whole |

The key to FIG. 5B is as follows:

| Lane No. | Sample |
|---|---|
| 1 | BRL |
| 2 | Blank |
| 3 | Fibrinogen Plasmin digest NR |
| 4 | Fibrin Plasmin digest NR |
| 5 | Fibrin MMP-3 (0.6 μg) super NR |
| 6 | Fibrin MMP-3 (0.6 μg) 24 hr prec NR |
| 7 | Fibrin MMP-3 (6 μg) super |
| 8 | Fibrin MMP-3 (6 μg) prec |
| 9 | Fibrin MMP-3 (6 μg) 48 hr whole NR |
| 10 | Fibrin MMP-3 (6 μg) 48 hr. whole NR TNE |

At 24 hours, with MMP-3 at 1:200 E:S ratio, fibrin is degraded into three fragments of molecular weight between 200 and 170 kDa (FIG. 5A, lane 5). The degraded fragments are released in the supernatants and retain MoAb/4-2 immunoreactivity (FIG. 5A, lane 6). At 24 hours, the γ dimer is being converted into a γ monomer (FIG. 5A, lane 7). At 48 hours most of the γ dimer has been monomerized (FIG. 5A, lanes 8,9). In FIG. 5B the same samples are shown under non-reducing conditions. Degradation of the D-dimer into a D monomer-like fragment is shown in FIG. 5B, lanes 8–9. Complete degradation is shown at 48 hours (FIG. 5B, lane 9).

Figure 6A:
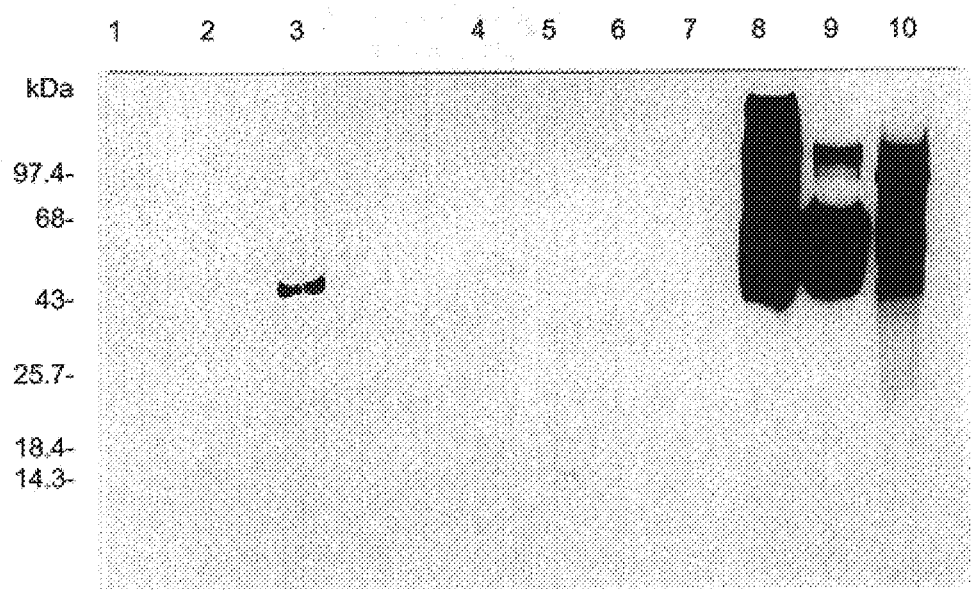
FIGS. 6A and 6B show short and long exposures, respectively, of an immunoblot of the degradation products of fibrin digestion by MMP-3 and plasmin, as measured with MoAb/T2G1 (B$\beta$ 15–42) and MoAb/1D4 (A$\alpha$ 349–406).
Figure 6B:
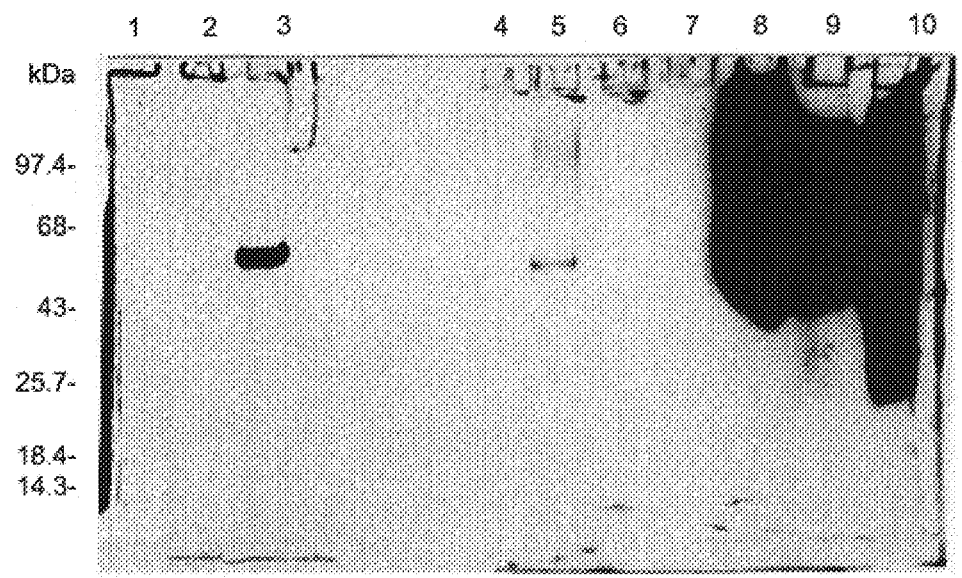

Immunoblot of the degradation products of fibrin digestion by MMP-3 and plasmin was performed using MoAb/T2G1 and MoAb/1D4 under reducing conditions, as shown in FIG. 6. The key to both of FIGS. 6A and 6B is as follows:

| Lane No. | Sample |
|---|---|
| 1 | Fibrin MMP-3 (0.6 µg) 24 hr |
| 2 | Fibrin MMP-3 (6 µg) 24 hr |
| 3 | Fibrin clot 24 hr |
| 4 | BRL |
| 5 | Fibrin MMP-3 (0.6 µg) 24 hr |
| 6 | Fibrin MMP-3 (6 µg) 24 hr |
| 7 | Fibrin MMP-3 (6 µg) 24 hr prec TNE |
| 8 | Fibrin clot 24 hr |
| 9 | Fibrinogen SR |
| 10 | Fibrin Plasmin digest SR |

(Note that FIGS. 6A and 6B are two different exposures of the same blot.)

MoAb/T2G1 is specific for Bβ 15–42, but only of fibrin II, not of fibrinogen/fibrin I. MoAb/1D4 is specific for Aα 349–406 in fibrinogen and fibrin, as well as in their plasmin digests. MoAb/T2G1 immunoreactivity is lost in the digests of fibrin by MMP-3 both at lower (1:200) and higher (1:20) concentration (FIG. 6, lanes 1–2), while it is present in intact fibrin (FIG. 6, lane 3). MoAb/1D4 immunoreactivity is still partially preserved in the fibrin digest at lower concentration of MMP-3 (FIG. 6, lane 5), but it is completely lost in digests at higher concentration of MMP-3 at both 24 and 48 hours (FIG. 6, lanes 6–7), while it is clearly present in the control samples (FIG. 6, lanes 8–10). This result means that Aα 349–406 (corresponding to CNBr fragment VIII, the region involved in the α-chain cross-linking) has been cleaved from fibrin by MMP-3.

EXAMPLE 6

Figure 7A:
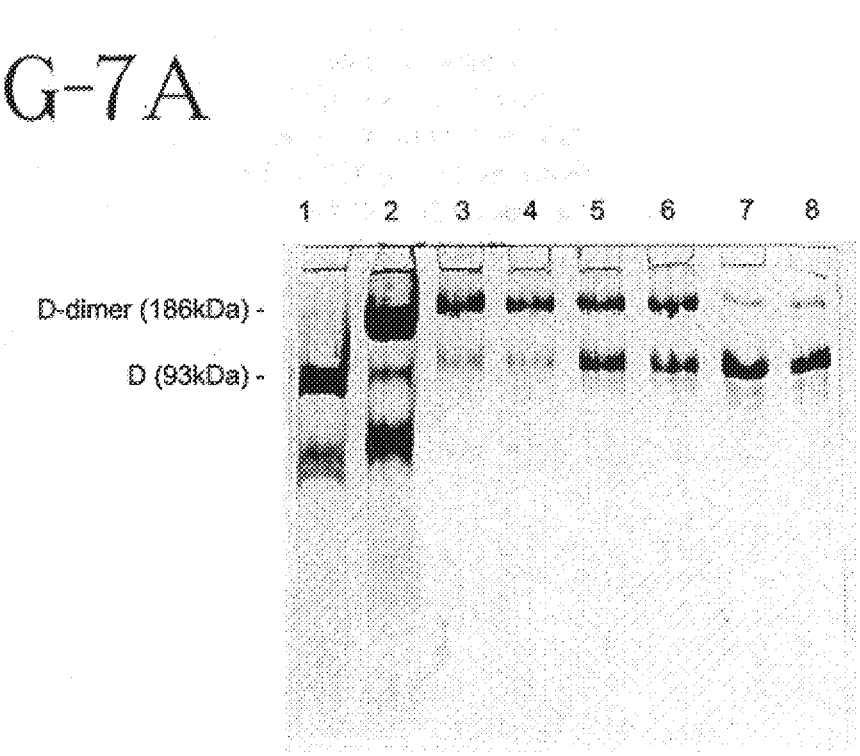
FIG. 7A shows an electrophoretic analysis of D dimer treated with MMP-3, showing time- and concentration-dependent degradation of D dimer by MMP-3.
Figure 7B:
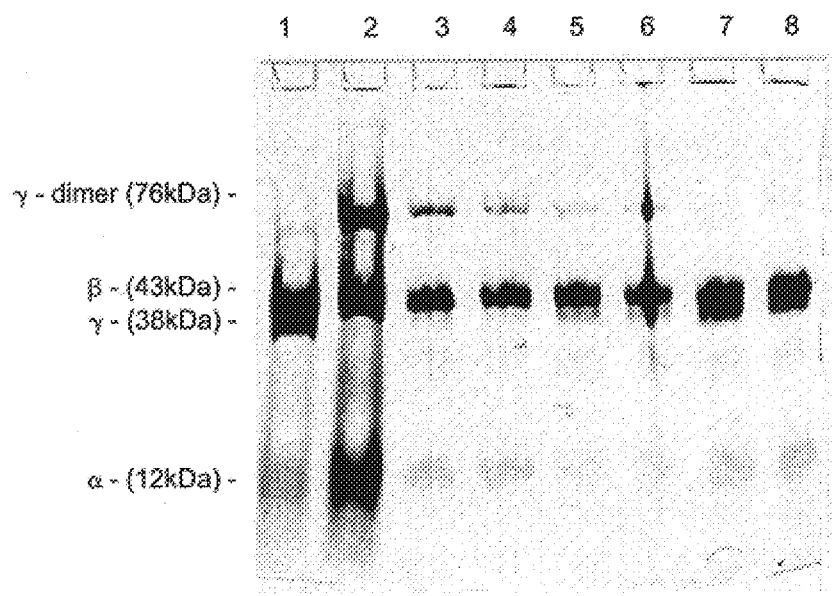
FIG. 7B shows an electrophoretic analysis of $\gamma$ dimer treated with MMP-3, showing time- and concentration-dependent degradation of $\gamma$ dimer by MMP-3.

Experiments were carried out to see whether MMP-3 would cleave purified D-dimer into D monomer. Purified fragment D and D-dimer were incubated 37° C. for 4 and 24 hours with lower (1:20) and higher (1:200) concentration of MMP-3. The digests were resolved on PAGE (7% phosphate). The samples were transferred to nitrocellulose membranes and stained. The results are shown in FIGS. 7A and 7B. Samples were run under reducing (FIG. 7A) and non-reducing (FIG. 7B) conditions. The key to FIGS. 7A and 7B is as follows:

| Lane No. | Sample |
|---|---|
| 1 | Plasmin digested fibrinogen (D monomer ~93 kDa) |
| 2 | Plasmin digested cross-linked fibrin (D-dimer ~186 kDa) |
| 3 | MMP-3 digest (0.6 µg enzyme/4 hrs) of pure D-dimer |
| 4 | MMP-3 digest (0.6 µg enzyme/4 hrs) of pure D-dimer |
| 5 | MMP-3 digest (6.0 µg enzyme/4 hrs) of pure D-dimer |
| 6 | MMP-3 digest (6.0 µg enzyme/4 hrs) of pure D-dimer |
| 7 | MMP-3 digest (6.0 µg enzyme/24 hrs) of pure D-dimer |
| 8 | MMP-3 digest (6.0 µg enzyme/24 hrs) of pure D-dimer |

In both FIGS. 7A and 7B, progressive degradation of D-dimer into D monomer is shown (lanes 3–8, samples are shown in duplicates). Also, as this gel was made 2 months after preparation of these samples, this proves that the reaction has been stopped effectively and has not progressed any further. The results indicate that monomerization occur even at 4 hours with the lower amount of enzyme (1:200). Increasing the amount of enzyme ten-fold increases the monomerization at 4 hours and almost completely converts the substrate at 48 hours. This is supported in FIG. 7B, which shows the conversion of γ dimer (~78 kDa) to γ monomer (~38 kDa).

EXAMPLE 7

Several ELISA binding assays were performed according to accepted methods. Plates were coated with different digests and assayed for antibody binding using MoAb/4A5. As noted above, this antibody is specifically reactive with an epitope in the γ chain cross-linking region (i.e., γ 397–411). The region identified by MoAb/4A5 is partly coincident and partly neighboring with the epitope detected by MoAb/4-2 (γ 392–406). The results of these assays are shown in Table III.

TABLE III

Summary of Binding - ELISA

| DIGESTS | MoAb/4-2 | MoAb/4A5 | MoAb/Ea3 | MoAb/TD 57-3 | MoA/Fd4 7B3 | MoAb/ID4 | MoAb/2N3H10 |
|---|---|---|---|---|---|---|---|
| MMP-3 | | | | | | | |
| (super) (0.6 µg) 24 hr 1:200 | 0.278* | 0.925 | 0.073 | 0.588 | 1.230* | 0.998 | 1.362 |
| (super) (0.6 µg) 24 hr 1:200 | 0.27 | 0.989 | 0.106 | 0.56 | 1.264 | 0.785 | 1.192* |
| (whole) (6.0 µg) 4 hr 1:20 | ∅ | ∅ | ∅ | ∅ | ∅ | 1.204 | <0.07 |
| (whole) (6.0 µg) 4 hr 1:20 | 0.212 | <0.07 | 0.097 | 0.072 | ∅ | 1.174 | 0.48 |
| (super) (6.0 µg) 24 hr 1:20 | 0.124 | ∅ | <0.07 | <0.07 | ∅ | 0.222 | 0.285 |
| (super) | 0.136 | ∅ | <0.07 | <0.07 | ∅ | 0.215 | 0.279 |

TABLE III-continued

Summary of Binding - ELISA

| DIGESTS | MoAb/4-2 | MoAb/4A5 | MoAb/Ea3 | MoAb/TD 57-3 | MoA/Fd4 7B3 | MoAb/ID4 | MoAb/2N3H10 |
|---|---|---|---|---|---|---|---|
| (6.0 μg) 24 hr 1:20 (whole) | 0.478 | Ø | 0.316 | 0.238 | Ø | Ø | 0.143 |
| (6.0 μg) 48 hr 1:20 (whole) | 0.133 | Ø | <0.07 | <0.07 | Ø | Ø | 0.149 |
| (6.0 μg) 48 hr 1:20 PLASMIN | | | | | | | |
| (whole) (0.15 μg) 24 hr 1:800 | 0.304 | 1.056 | 0.174 | 0.394 | 1.05 | 1.23 | 1.211 |
| (whole) (0.15 μg) 24 hr 1:800 MMP-3/TNE | 0.321 | 1.084 | 0.209 | 0.384 | 1.083 | 1.232 | 1.272 |
| (whole) (6.0 μg) 48 hr 1:20 PLASMIN | <0.07 | Ø | Ø | Ø | Ø | 0.123 | 0.382 |
| (whole) (0.15 μg) 24 hr 1:800 | 0.294 | 1.019 | 0.18 | 0.377 | 1.154 | 1.272 | 1.321* |

*Single value or poor double value
For each antibody Clone Culture Fluid was used Table III shows that a loss of MoAb/4A5 epitope occurs with increasing concentration of MMP-3. This means that the fibrinogen cleavage site of MMP-3 is in the region of this epitope (the cross-links occur in the region gly397-lys406). This type of cleavage does not occur with plasmin, as can be clearly seen from Table III. In MMP-3 digests, there is progressive loss of core fragments D and E, as recognized by antibodies FD4-7B3 and 2N3H10, respectively. There is no loss of either of these conformation epitopes in the plasmin digests. These results are independent of the two buffers used for diluting purified fibrinogen, i.e., the MMP activation buffer or TNE buffer (0.05M Tris-HCl (pH 7.4), containing 0.1M NaCl, 0.001M EDTA and 100 KIU/ml aprotinin).

The epitope of the antibody 1D4 is also clearly modified and will be further investigated in competition ELISA assay. The results shown in FIGS. 6A and 6B (lanes 4–10) suggest that this epitope occurs on a smaller molecular weight degraded fragment that may not bind well to the plastic, resulting in an inability of the antibody to see it.

Inasmuch as MMP-3 cleaves at just the site at which fibrin cross-linking occurs, a strong teleological argument is readily made that MMP-3 plays a singular role in fibrinolysis. Coordinated regulation of the metalloproteinases and plasminogen activators could, therefore, result in synergistic effects and complete degradation of both the extracellular matrix and the fibrin meshwork resulting from wound healing, inflammation, thrombosis, cancer, renal disease, or other pathophysiological processes. Accordingly, it is contemplated that the co-administration of MMP-3 with another thrombolytic agent such as t-PA would also achieve a synergistic therapeutic effect, in which each component complements or potentiates the other.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

REFERENCES

1. Francis C. W., and Marder V. J., "Physiologic regulation and pathologic disorders of fibrinolysis", Chapter 54 in *Hemostasis and Thrombosis: Basic Principles and Clinical Practice*, 3rd ed., Colman R. W., Hirsh J., Marder V. J., and Salzman E. W., eds., J. B. Lippincott Co, Philadelphia (1994).
2. Collen D., "On the regulation and control of fibrinolysis", *Thromb Haemost* 43:77–89 (1980).
3. Collen D., and Lijnen H. R., "Basic and clinical aspects of fibrinolysis and thrombolysis", *Blood* 3114–24 (1991).
4. Murphy G., Atkinson S., Ward R., Gavrilovic J., and Reynolds J. J., "The role of plasminogen activators in the regulation of connective tissue metalloproteinases", *Ann NY Acad Sci*, 667:1–12 (1992).
5. Brakman P., and Kluft C., eds., *Plasminogen Activation in Fibrinolysis, in Tissue Remodeling, and in Development*, Ann NY Acad Sci, vol. 667 (1992).
6. Martin G. V., Kennedy J. W., and Marder V. J., "Thrombolytic therapy for coronary artery disease", Chapter 73 in *Hemostasis and Thrombosis: Basic Principles and Clinical Practice*, 3rd ed., Colman R. W., Hirsh J., Marder V. J., and Salzman E. W., eds., J. B. Lippincott Co, Philadelphia (1994).
7. Sobel B. E., Collen D., and Grossbard E. B., eds., *Tissue Plasminogen Activator in Thrombolytic Therapy*, Marcel Dekker, Inc., New York (1987).
8. Collen D., "Biological properties of plasminogen activators", Chapter 1 in Sobel B. E., Collen D., and Grossbard E. B., eds., *Tissue Plasminogen Activator in Thrombolytic Therapy*, Marcel Dekker, Inc., New York (1987).

9. Lee S. W., Kahn M. L., and Dichek D. A., "Control of clot lysis by gene transfer", *Trends Cardiovasc Med* 3:61–66 (1993).
10. Purves L., Purves M., and Brandt W., "Cleavage of fibrin-derived D-dimer into monomers by endopeptidase from puff adder venom (*Bitis arietans*) acting at cross-linked sites of the γ-chain. Sequence of carboxy-terminal cyanogen bromide γ-chain fragments", *Biochemistry* 26:4640–46 (1987).
11. Retzios A. D., and Markland F. S. Jr., "Purification, characterization, and fibrinogen cleavage sites of three fibrinolytic enzymes from the venom of *Crotalus basiliscus basiliscus*", *Biochemistry* 31:4547–57 (1992).
12. Sanchez E. F., Magalhes A., Mandelbaum F. R., and Diniz C. R., "Purification and characterization of the hemorrhagic factor II from the venom of the Bushmaster snake (*Lachesis muta muta*)", *Biochim Biophys Acta* 1074:347–56 (1991).
13. Nagase H., Barrett A. J., and Woessner J. F. Jr., "Nomenclature and glossary of the matrix metalloproteinases", *Matrix, Supplement* 1:421–24 (1992).
14. Zavalova L. L., Kuzina E. V., Levina N. B., and Baskova I. P., "Monomerization of fragment DD by destabilase from the medicinal leech does not alter the N-terminal sequence of the γ-chain", *Thrombosis Res* 71:241–44 (1993).
15. Budzynski A. Z., "Interaction of hementin with fibrinogen and fibrin", *Blood Coagulation and Fibrinolysis* 2:149–52 (1991).
16. Loewy A. G., Santer U. V., Wieczorek M., Blodgett J. K., Jones S. W., and Cheronis J. C., "Purification and characterization of a novel zinc-proteinase from cultures of *Aeromonas hydrophila*", *J Biol Chem* 268:9071–78 (1993).
17. Cawston T., "Metalloproteinase inhibitors—Crystal gazing for a future therapy", *Br J Rheumatol* 30:242–44 (1991).
18. Kleiner D. E. Jr., and Stetler-Stevenson W. G., "Structural biochemistry and activation of matrix metalloproteinases", *Curr Opin Cell Biol* 5:891–97 (1993).
19. Matrisian L. M., "The matrix-degrading metalloproteinases", *BioEssays* 14:455–63 (1992).
20. Nagase H., Enghild J. J., Suzuki K., and Salvesen G., "Stepwise activation mechanisms of the precursor of matrix metalloproteinase 3 (stromelysin) by proteases and (4-aminophenyl)mercuric acetate", *Biochemistry* 29:5783–89 (1990).
21. Nagase H., Ogota Y., Suzuki K., Enghild J. J., and Salvesen G., "Substrate specificities and activation mechanisms of matrix metalloproteinases", *Biochem Soc Trans* 19:715–18 (1991).
22. Henney A. M., Wakeley P. R., Davies M. J., Foster K., Hembry R., Murphy G., and Humphries S., "Localization of stromelysin gene expression in atherosclerotic plaques by in situ hybridization", *Proc Natl Acad Sci USA* 88:8154–58 (1991).
23. Galis Z. S., Sukhova G. K., Lark M. W., and Libby P., "Increased expression of matrix metalloproteinases and matrix degrading activity in vulnerable regions of human atherosclerotic plaques", *J. Clin Invest* 94:2493–2503 (1994).
24. Doolittle R. F., "Fibrinogen and fibrin", in Bloom A. L., and Thomas D. P., eds., *Hemostasis and Thrombosis* Churchill Livingston, Edinburgh, N.Y. (1987).
25. Fu Y., and Grieninger G., "$Fib_{420}$: A normal human variant of fibrinogen with two extended α chains", *Proc Natl Acad Sci USA* 91:2625–28 (1994).
26. Gabriel D. A., Muga K., and Boothroyd E. M., "The effect of fibrin structure on fibrinolysis", *J Biol Chem* 267:24259–63 (1992).
27. Kudryk B. J., Grossman Z. D., McAfee J. G., and Rosebrough S. F., "Monoclonal antibodies as probes for fibrin(ogen) proteolysis", Chapter 19 in *Monoclonal Antibodies in Immunoscintigraphy*, Chatal J-F, ed., CRC Press, Boca Raton (1989).
28. Glick B. R., and Pasternak J. J., *Molecular Biotechnology: Principles and Applications of Recombinant DNA*, Chapter 17, pp. 403–20 (1994).
29. Bini A., Callender S., Pocyk R., Blombäck B., and Kudryk B. J., "Flow and antibody binding properties of hydrated fibrins prepared from plasma, platelet rich plasma and whole blood", *Thrombosis Res* 76:145–56 (1994).
30. Okada Y., Nagase H., and Harris E. D., Jr., "A metalloproteinase from human rheumatoid synovial fibroblasts that digests connective tissue matrix components", *J Biol Chem* 261:14245–55 (1986).
31. Laemmli U. K., and Favre M., "Maturation of the head of bacteriophage T4. I. DNA packaging events", *J Mol Biol* 80:575–99 (1973).
32. McDonagh J., Messel H., McDonagh R. P., Jr., Murano G., and Blomback B., "Molecular weight analysis of fibrinogen and fibrin chains by an improved sodium dodecyl sulfate gel electrophoresis method", *Biochim Biophys Acta* 257:135–42 (1972).

What is claimed is:

1. A method of degrading fibrin(ogen), comprising:
contacting said fibrin(ogen) with an effective amount of a fibrinolytic matrix metalloproteinase.

2. The method of claim 1, wherein said fibrinolytic matrix metalloproteinase is endogenous to a mammal.

3. The method of claim 1, wherein said fibrinolytic matrix metalloproteinase is a stromelysin.

4. The method of claim 1, wherein said fibrinolytic matrix metalloproteinase is matrix metalloproteinase-3 (MMP-3).

5. The method of claim 1, wherein said method further comprises:
contacting said fibrin(ogen) with an effective amount of an adjunct composition comprising at least one adjunct compound having activity in fibrinolysis.

6. The method of claim 5, wherein said adjunct composition comprises a plasminogen activator, hirudin, an enzyme inhibitor, an anticoagulant, or a combination thereof.

7. The method of claim 6, wherein said adjunct composition comprises a urokinase-plasminogen activator (u-PA), a tissue-type plasminogen activator (t-PA), a streptokinase, a staphylokinase, or a combination thereof.

8. The method of claim 1, wherein said method is performed ex vivo.

9. The method of claim 1, wherein said method is performed in vivo.

10. A method of fibrinolytic therapy, comprising:
administering to a subject in need of fibrinolytic therapy a therapeutically effective amount of a fibrinolytic matrix metalloproteinase.

11. The method of claim 10, wherein said fibrinolytic matrix metalloproteinase is endogenous to the species of the subject.

12. The method of claim 10, wherein said fibrinolytic matrix metalloproteinase is a stromelysin.

13. The method of claim 10, wherein said fibrinolytic matrix metalloproteinase is matrix metalloproteinase-3 (MMP-3).

14. The method of claim 10, wherein said method further comprises:

administering to said subject a therapeutically effective amount of an adjunct composition comprising at least one adjunct compound having activity in fibrinolysis.

15. The method of claim 14, wherein said adjunct composition comprises a plasminogen activator, hirudin, an enzyme inhibitor, an anticoagulant, or a combination thereof.

16. The method of claim 15, wherein said adjunct composition comprises a urokinase-plasminogen activator (u-PA), a tissue-type plasminogen activator (t-PA), a streptokinase, a staphylokinase, or a combination thereof.

17. A composition for thrombolytic therapy, comprising:

a fibrinolytic matrix metalloproteinase, at least one adjunct compound having activity in fibrinolysis, and a pharmaceutically acceptable carrier.

18. The composition of claim 17, wherein said fibrinolytic matrix metalloproteinase is endogenous to a mammal.

19. The composition of claim 17, wherein said fibrinolytic matrix metalloproteinase is a stromelysin.

20. The composition of claim 17, wherein said fibrinolytic matrix metalloproteinase is matrix metalloproteinase-3 (MMP-3).

21. The composition of claim 17, wherein said composition comprises a plasminogen activator, hirudin, an enzyme inhibitor, an anticoagulant, or a combination thereof.

22. The composition of claim 21, wherein said composition comprises a urokinase-plasminogen activator (u-PA), a tissue-type plasminogen activator (t-PA), a streptokinase, a staphylokinase, or a combination thereof.

23. A kit for performing thrombolytic therapy, comprising: a composition comprising a fibrinolytic matrix metalloproteinase, at least one adjunct composition comprising at least one adjunct compound having activity in fibrinolysis, and a container.

24. The kit of claim 23, wherein said fibrinolytic matrix metalloproteinase is endogenous to mammal.

25. The kit of claim 23, wherein said fibrinolytic matrix metalloproteinase is a stromelysin.

26. The kit of claim 23, wherein said fibrinolytic matrix metalloproteinase is matrix metalloproteinase-3 (MMP-3).

27. The kit of claim 23, wherein said adjunct composition comprises a plasminogen activator, hirudin, an enzyme inhibitor, an anticoagulant, or a combination thereof.

28. The kit of claim 27, wherein said adjunct composition comprises a urokinase-plasminogen activator (u-PA), a tissue-type plasminogen activator (t-PA), a streptokinase, a staphylokinase, or a combination thereof.

29. The kit of claim 23, further comprising means for administering a therapeutically effective amount of said composition.

30. The kit of claim 29, wherein said administering means includes means for administering said composition parenterally.

\* \* \* \* \*